(12) United States Patent
Lawter et al.

(10) Patent No.: US 7,976,489 B2
(45) Date of Patent: Jul. 12, 2011

(54) DEVICE FOR DELIVERING MEDICINAL IMPLANTS

(75) Inventors: James R. Lawter, Yardley, PA (US); Zhangwen Wu, New Hope, PA (US); Michael J. Rello, Harleysville, PA (US); Charles D. Faust, Bensalem, PA (US); Erik deBrun, Philadelphia, PA (US)

(73) Assignee: OraPharma, Inc., Warminster, PA (US)

( * ) Notice: Subject to any disclaimer, the term of this patent is extended or adjusted under 35 U.S.C. 154(b) by 0 days.

(21) Appl. No.: 12/326,431

(22) Filed: Dec. 2, 2008

(65) Prior Publication Data

US 2009/0142727 A1    Jun. 4, 2009

Related U.S. Application Data

(60) Provisional application No. 60/992,193, filed on Dec. 4, 2007.

(51) Int. Cl.
*A61M 31/00* (2006.01)
(52) U.S. Cl. ......................................................... 604/63
(58) Field of Classification Search .............. 604/57–64; 433/80, 89, 90
See application file for complete search history.

(56) References Cited

U.S. PATENT DOCUMENTS

| | | | |
|---|---|---|---|
| 1,347,622 A | 7/1920 | Deinnger | |
| 3,625,208 A | 12/1971 | Frost et al. | |
| 3,638,314 A | 2/1972 | Lopez | |
| 3,990,152 A | 11/1976 | Hirdes | |
| 4,079,518 A | 3/1978 | Marshall | |
| 4,092,778 A | 6/1978 | Hirdes | |
| 4,105,030 A * | 8/1978 | Kercso | 604/506 |
| 4,165,800 A | 8/1979 | Doherty et al. | |
| 4,175,326 A | 11/1979 | Goodson | |
| 4,377,380 A | 3/1983 | Vadas | |
| 4,400,170 A * | 8/1983 | McNaughton et al. | 604/62 |
| 4,431,414 A | 2/1984 | Lawrence | |
| 4,479,781 A | 10/1984 | Herold | |
| 4,560,352 A | 12/1985 | Neumiester | |
| 4,581,022 A | 4/1986 | Leonard et al. | |
| 4,641,766 A | 2/1987 | Vlasich | |
| 4,658,993 A | 4/1987 | Vlasich | |
| 4,680,027 A | 7/1987 | Parsons et al. | |
| 4,693,684 A | 9/1987 | Blatherwick | |
| 4,726,769 A | 2/1988 | Hirdes | |
| 4,732,302 A | 3/1988 | Muhlbauer | |
| 4,768,955 A | 9/1988 | Hirdes | |
| 4,784,607 A | 11/1988 | Francois | |
| 4,801,263 A | 1/1989 | Clark | |
| 4,813,602 A | 3/1989 | Corey | |
| 4,813,871 A | 3/1989 | Friedman | |
| 4,863,072 A | 9/1989 | Perler | |
| 4,871,094 A | 10/1989 | Gall | |

(Continued)

*Primary Examiner* — Nicholas D Lucchesi
*Assistant Examiner* — Nathan R Price
(74) *Attorney, Agent, or Firm* — Pepper Hamilton LLP

(57) ABSTRACT

The invention includes a device for inserting a medicament within a body cavity of a mammal, the device including a cartridge for containing the medicament therein, the cartridge including a housing, a retractable chamber disposed within the housing and having a lumen, a substantially stationary member disposed within the lumen of the retractable chamber and having a uniform cross-section sized to provide a sliding fit within the lumen to provide for retraction of the retractable chamber about the substantially stationary member upon actuation of the device, and means for retracting the retractable chamber about the substantially stationary member while maintaining the substantially stationary member in a substantially stationary position upon actuation of the device; the device further including means for activating the means for retracting the retractable chamber.

15 Claims, 26 Drawing Sheets

U.S. PATENT DOCUMENTS

| | | |
|---|---|---|
| 4,909,788 A | 3/1990 | Egolf |
| 4,993,948 A | 2/1991 | Cameron et al. |
| 4,995,540 A | 2/1991 | Colin |
| 5,000,886 A | 3/1991 | Lawter |
| 5,004,124 A | 4/1991 | Stefaniak et al. |
| 5,112,307 A | 5/1992 | Haber et al. |
| 5,129,825 A | 7/1992 | Discko, Jr. |
| 5,137,181 A | 8/1992 | Keller |
| 5,143,661 A | 9/1992 | Lawter |
| 5,236,355 A | 8/1993 | Brizzolara |
| 5,244,388 A | 9/1993 | Frush |
| 5,250,026 A | 10/1993 | Ehrlich et al. |
| 5,273,532 A * | 12/1993 | Niezink et al. .................. 604/62 |
| 5,286,257 A | 2/1994 | Fischer |
| 5,297,698 A | 3/1994 | Martin |
| 5,306,147 A | 4/1994 | Dragan |
| 5,322,511 A | 6/1994 | Armbruster et al. |
| 5,328,367 A | 7/1994 | Johnson |
| 5,366,733 A | 11/1994 | Brizzolara |
| 5,500,228 A | 3/1996 | Lawter |
| 5,622,498 A | 4/1997 | Brizzolara |
| 5,626,473 A | 5/1997 | Muhlbauer et al. |
| 5,722,829 A | 3/1998 | Wilcox |
| 5,743,431 A | 4/1998 | Brattesani |
| 5,743,436 A | 4/1998 | Wilcox |
| 5,755,362 A | 5/1998 | Rodriguez, Jr. |
| 5,782,633 A | 7/1998 | Muhlbauer |
| 5,783,205 A | 7/1998 | Berggren et al. |
| 5,800,169 A | 9/1998 | Muhlbauer |
| 5,865,804 A | 2/1999 | Bachynsky |
| 5,871,355 A | 2/1999 | Dragan et al. |
| 5,947,728 A | 9/1999 | Riebl |
| 6,047,864 A | 4/2000 | Winkler |
| 6,083,002 A | 7/2000 | Martin et al. |
| 6,234,795 B1 | 5/2001 | Fischer |
| 6,268,000 B1 | 7/2001 | Romer |
| 6,296,484 B1 | 10/2001 | Nihel |
| RE37,439 E | 11/2001 | Firth et al. |
| 6,319,002 B1 | 11/2001 | Pond |
| 6,334,774 B1 | 1/2002 | Mark |
| 6,494,715 B1 | 12/2002 | Riebl |
| 6,500,001 B2 | 12/2002 | Horth |
| 6,585,696 B2 | 7/2003 | Petersen |
| 6,612,465 B2 | 9/2003 | Pierson |
| 6,648,641 B1 | 11/2003 | Viltro |
| 6,682,348 B2 | 1/2004 | Lawter |
| 6,752,798 B2 | 6/2004 | McWethy |
| 6,802,822 B1 | 10/2004 | Dodge |
| 6,843,652 B2 | 1/2005 | Xie |
| 7,014,462 B1 | 3/2006 | Tilse |
| 7,033,343 B2 | 4/2006 | McWethy et al. |
| 7,198,485 B2 | 4/2007 | Hamman |
| 2003/0186190 A1 | 10/2003 | Lokhandwala |
| 2003/0186191 A1 | 10/2003 | Lawter et al. |
| 2004/0152042 A1 | 8/2004 | Lawter |
| 2004/0225322 A1 | 11/2004 | Garrison et al. |
| 2005/0202365 A1 | 9/2005 | Cao |
| 2007/0027469 A1 | 2/2007 | Smith et al. |

* cited by examiner

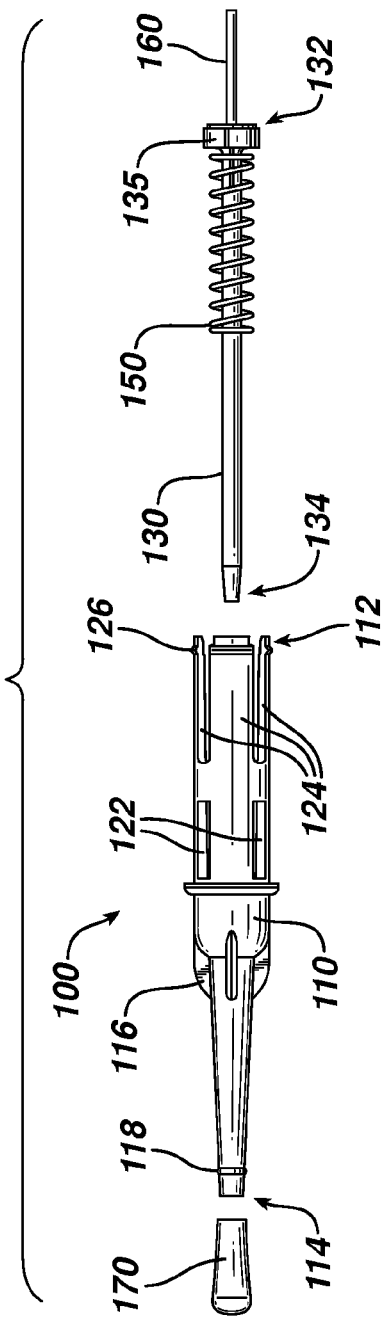
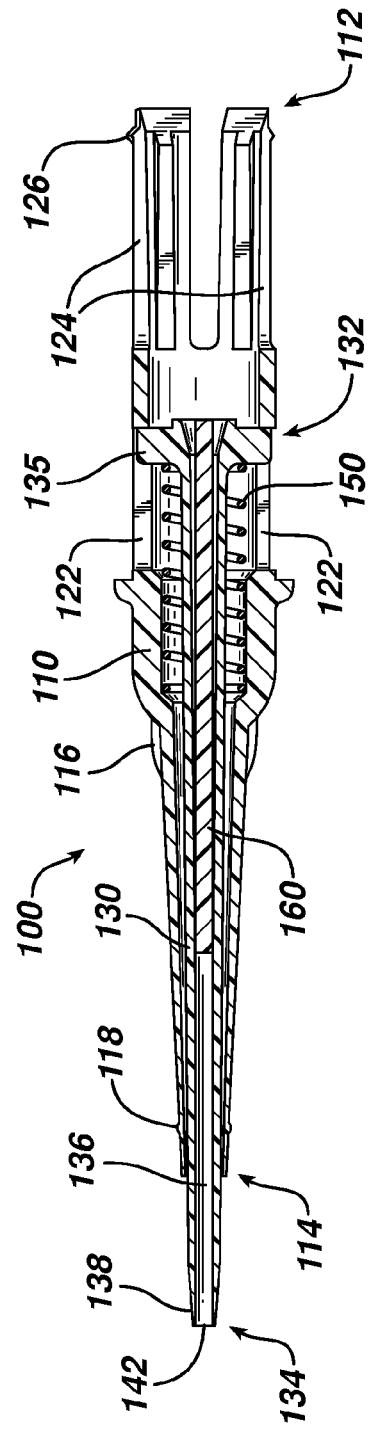

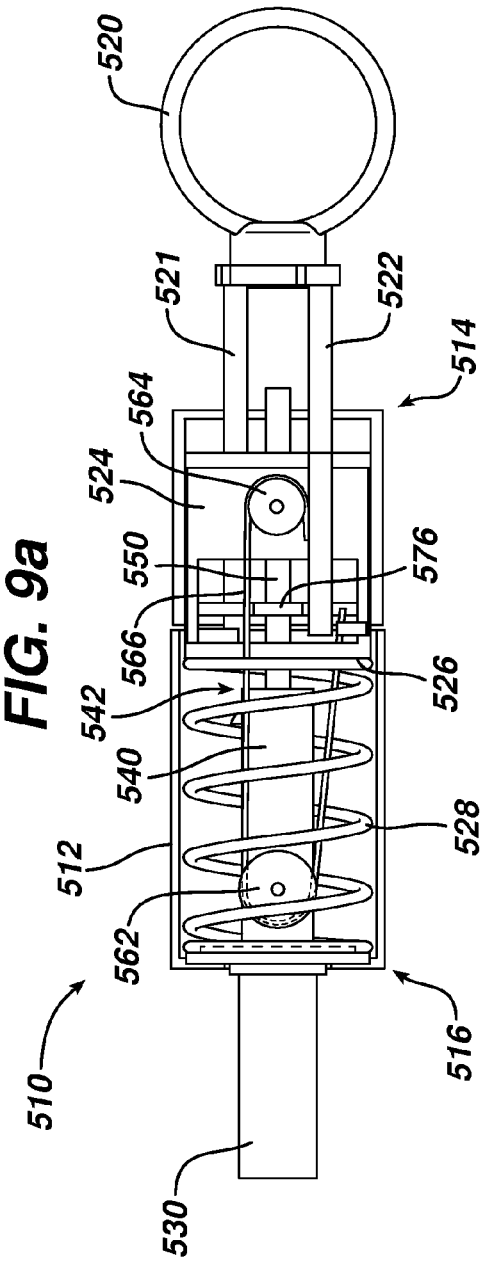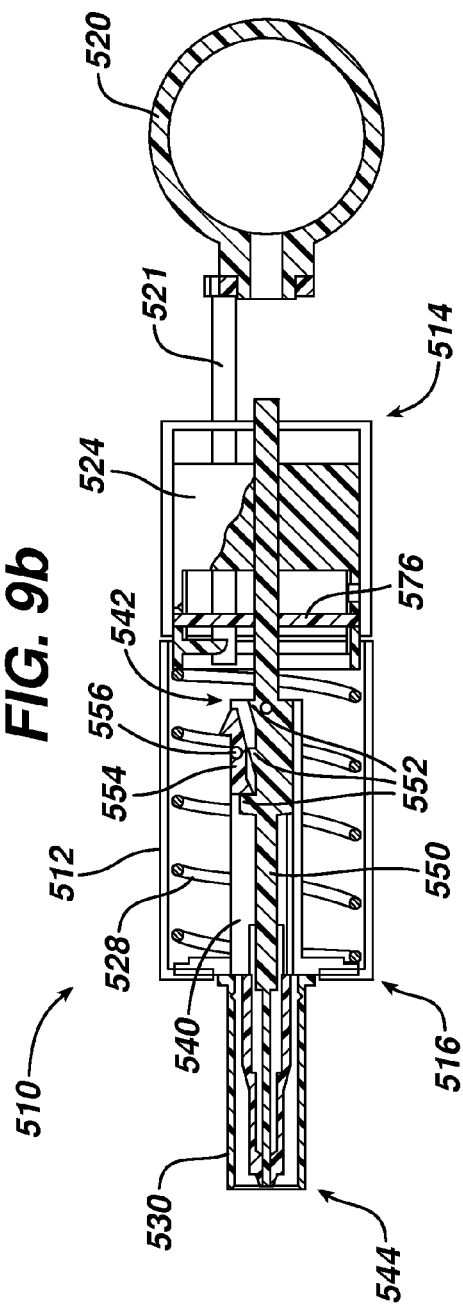

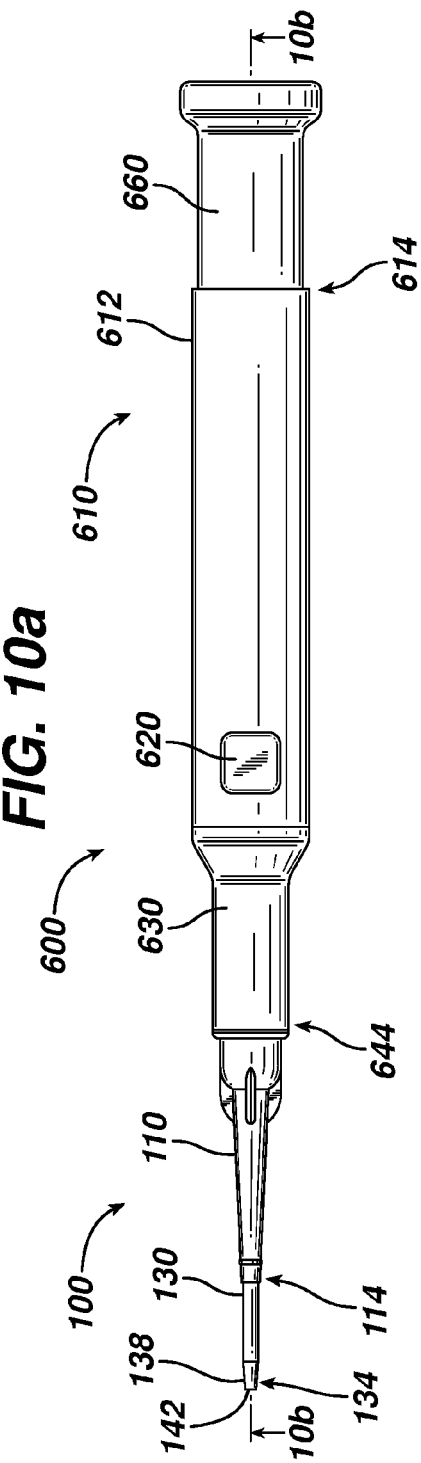
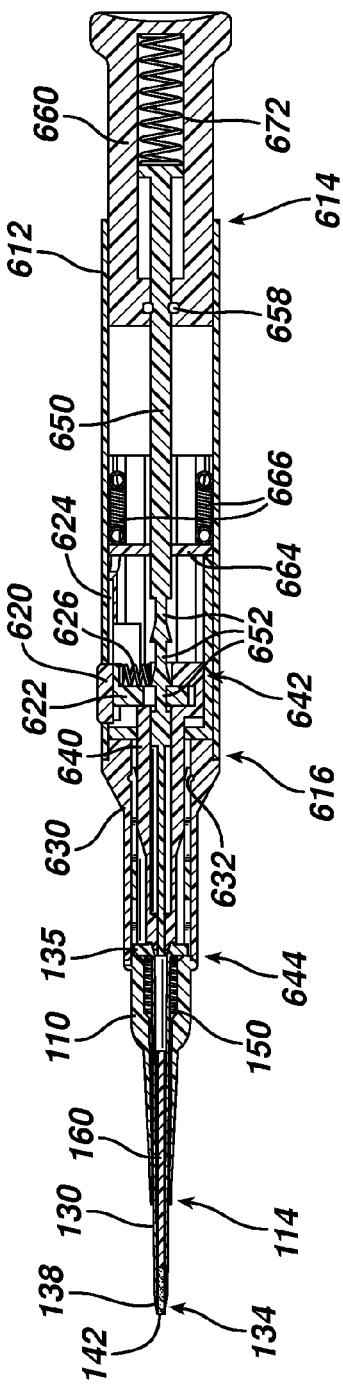
FIG. 10a
FIG. 10b

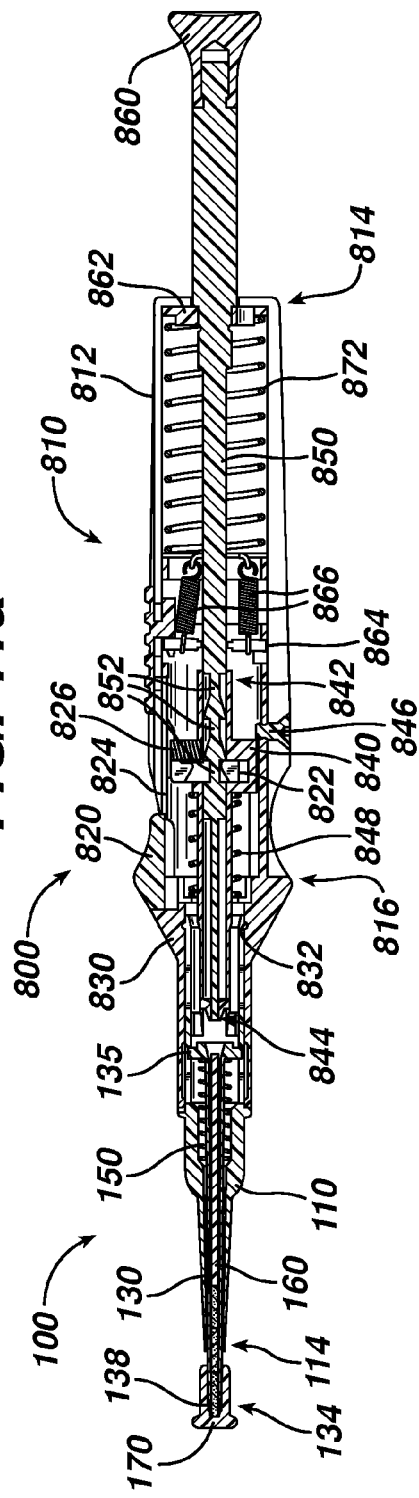
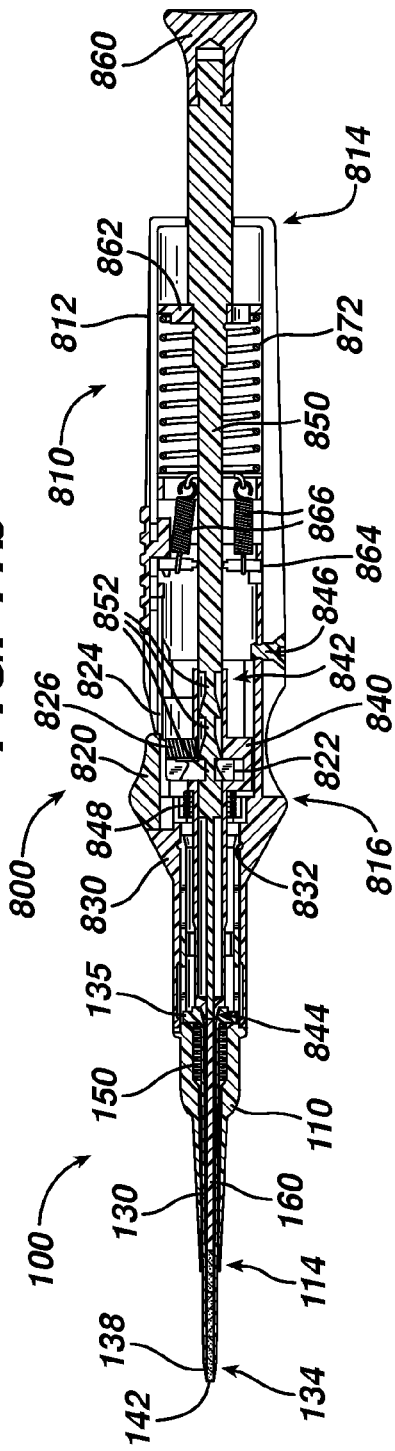

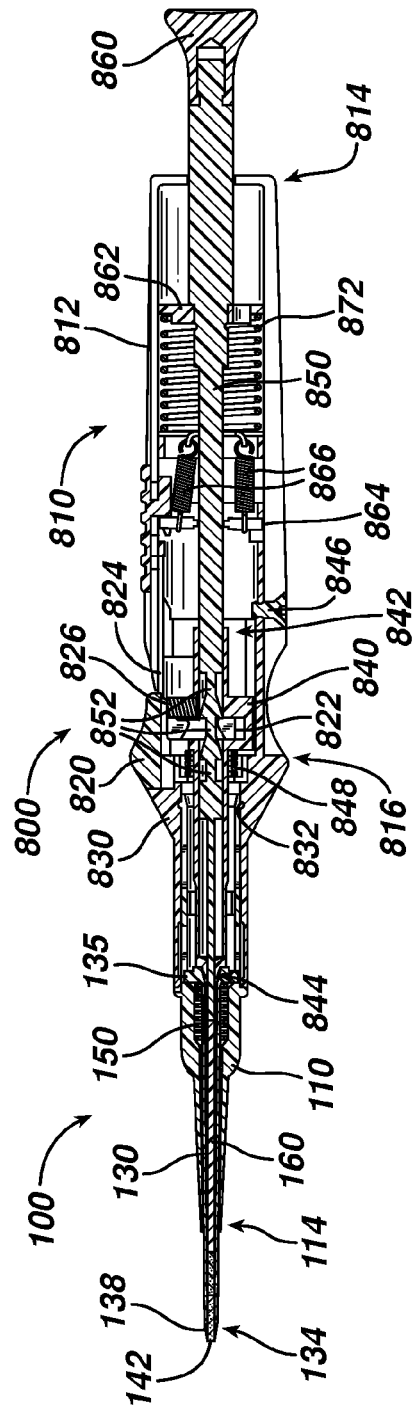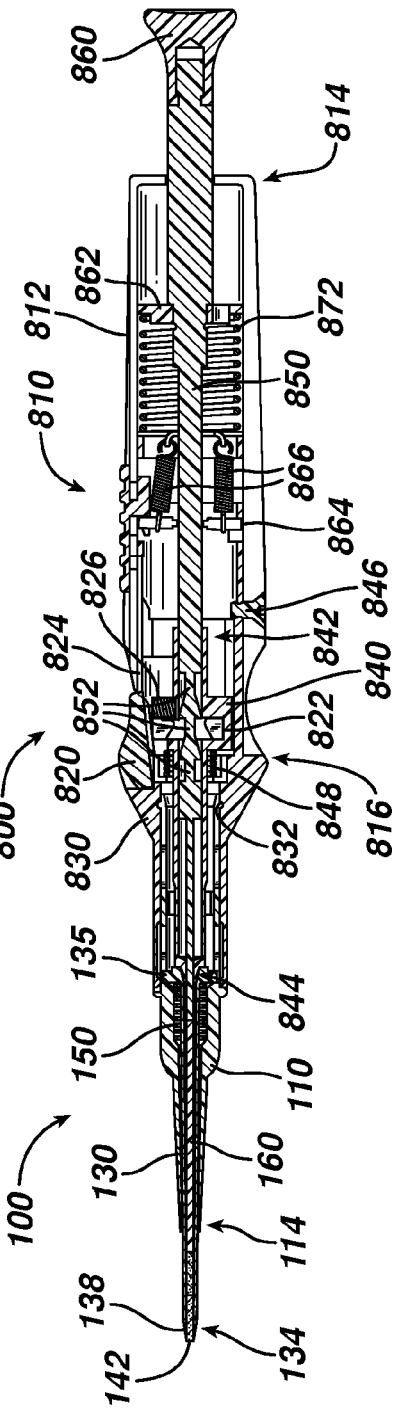

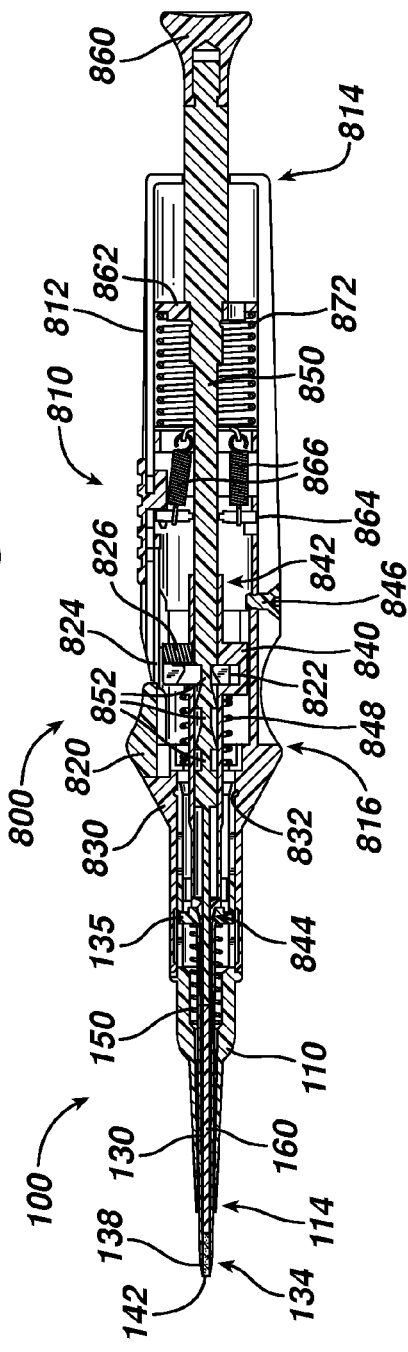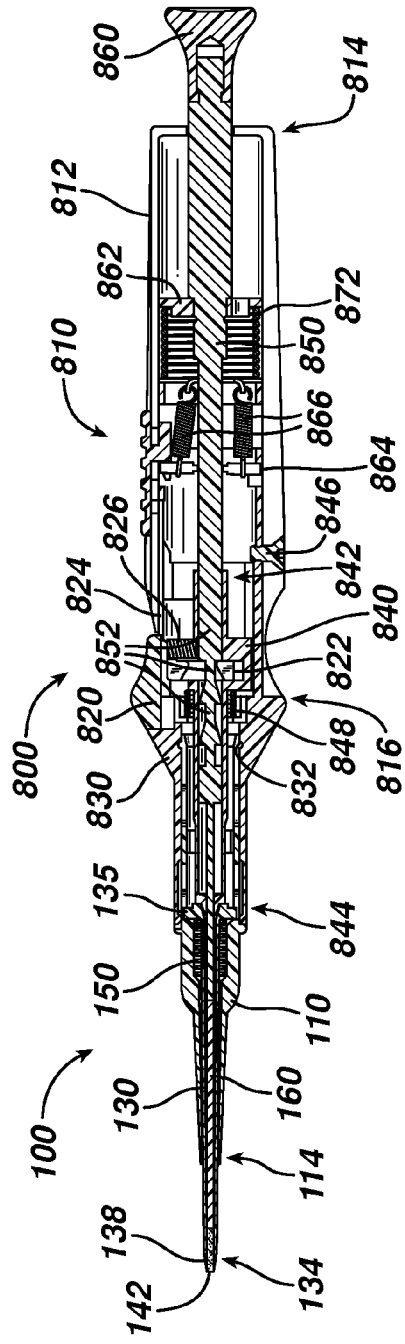

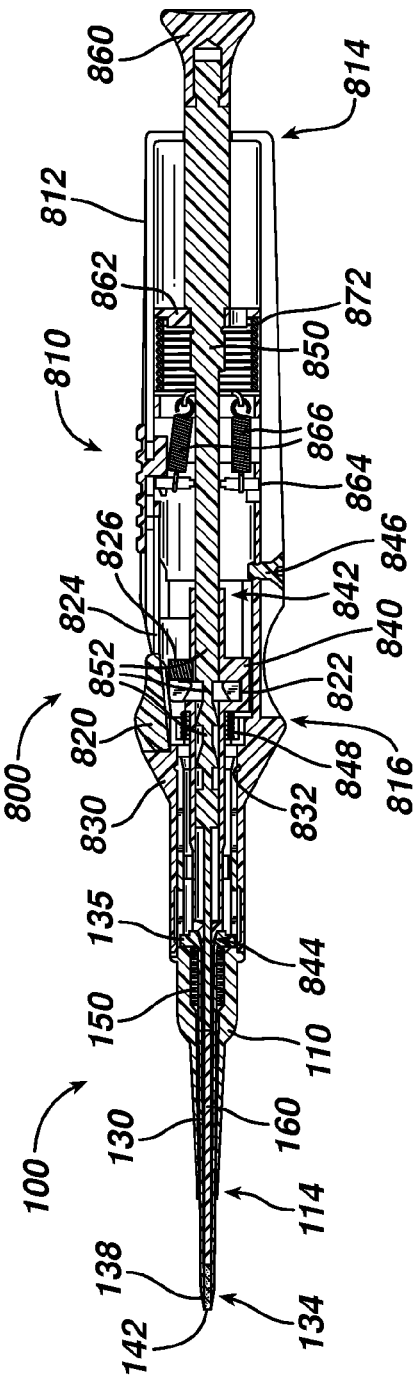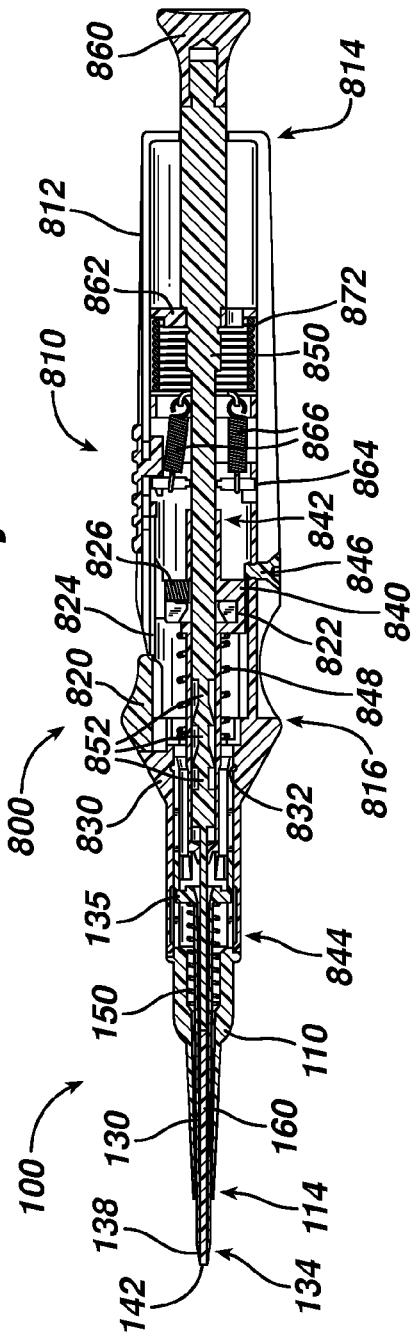

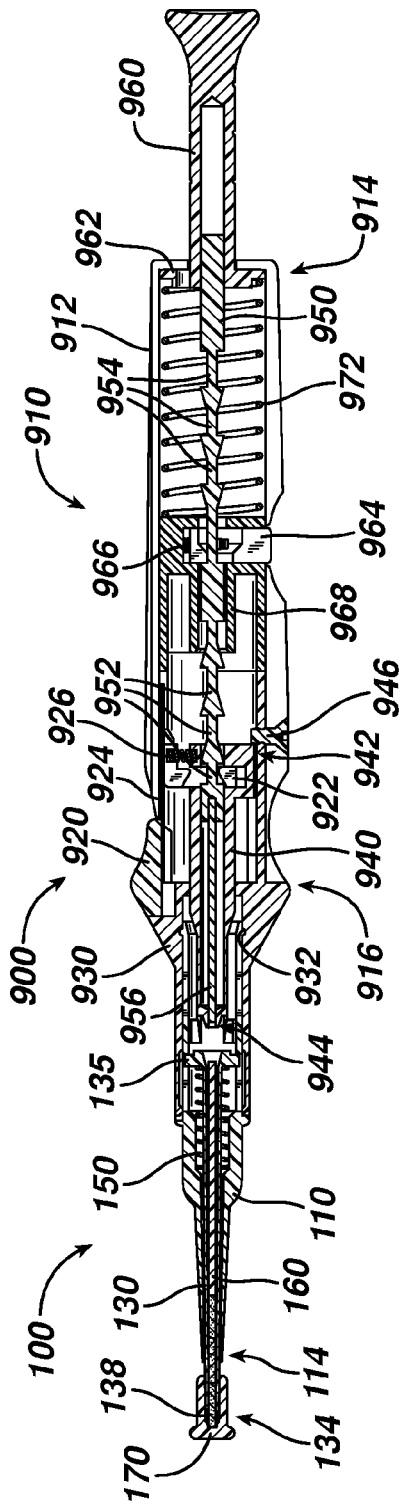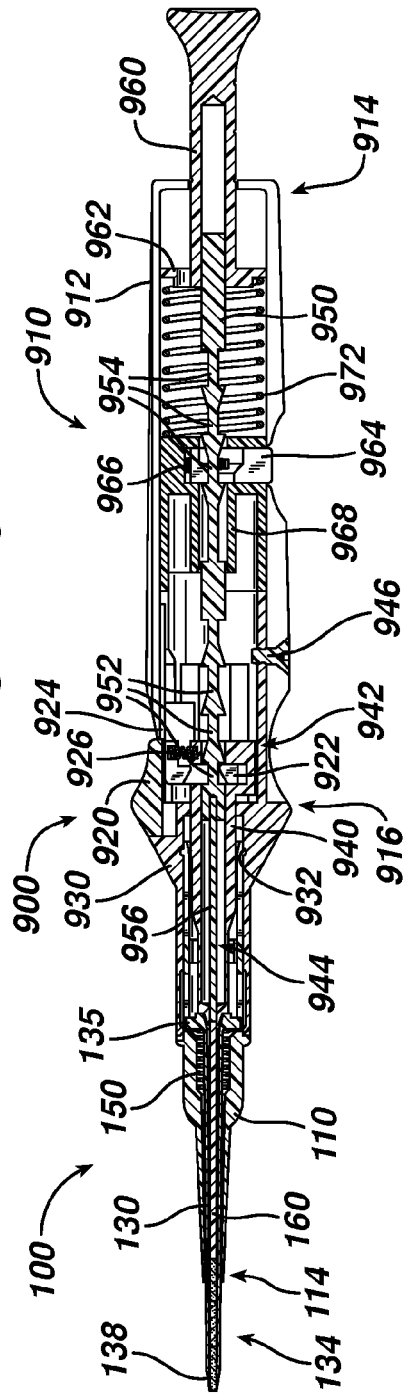
FIG. 12a
FIG. 12b

DEVICE FOR DELIVERING MEDICINAL IMPLANTS

CROSS REFERENCE TO RELATED APPLICATIONS

This application claims the benefit of U.S. provisional application 60/992,193 filed on Dec. 4, 2007, the complete disclosure of which is hereby incorporated herein by reference for all purposes.

FIELD OF THE INVENTION

The present invention relates to a device for inserting a medicament into a cavity of a mammal.

BACKGROUND OF THE INVENTION

Periodontal disease is a general term for a variety of dental conditions associated with either gingivitis or periodontitis. Gingivitis is an inflammation of the gingiva, or gums. It is commonly associated with poor oral hygiene and/or the hormonal state of the patient. If left untreated, gingivitis may develop into periodontitis.

Periodontitis is a bacterial disease in which the infection has progressed to involve the oral tissues that retain the teeth in the jawbone. With this disease the gums become red and inflamed. This condition, if untreated, results in damage to the ligaments and bone holding the teeth in place, and formation of pockets around the teeth. As the pockets become deeper, teeth loosen, to a point where they may fall out. Dental practitioners determine the severity of periodontitis, by measuring the depth of these pockets and reviewing x-rays of the teeth and surrounding bone.

Periodontal disease involves a different treatment protocol than other oral diseases. While many oral diseases can be treated with proper hygiene, fluoride, pastes, washes and rinses, periodontal disease is often resistant to this treatment. This is because of differences between the oral and periodontal cavities. The oral cavity is essentially an aerobic environment, constantly perfused by saliva. In contrast, the periodontal cavity is more anaerobic, and is perfused by plasma filtrate, known as "crevicular fluid". The growth of microorganisms within the periodontal cavity microenvironment may cause periodontal disease. As the disease progresses, the periodontal microenvironment becomes more anaerobic, and the flow of crevicular fluid increases.

Efforts to treat periodontal disease have met with limited degrees of success. This is because the site of the bacterial infections in the periodontal cavity are largely inaccessible to agents present in the oral cavity as well as agents provided to the oral cavity, such as mouthwashes, rinses and the like. Moreover, the increased outflow of crevicular fluid that accompanies periodontal disease inhibits therapeutic agents placed into the oral cavity from entering the pockets.

Oral systemic administration of antibiotics has been shown to be a useful method of controlling subgingival flora in some cases. However, because of side effects, such as those of the digestive system, oral systemic administration has had only limited use in treating periodontal disease. Oral systemic therapy also requires frequent dosing; so patient compliance is frequently a problem.

Recently, efforts have focused on delivering therapeutic agents directly to these pockets, in some cases, in a controlled release formulation. In general, administration of agents directly to the pocket permits higher local drug concentrations that can be safely achieved by systemic administration. Also, some agents such as growth factors must be administered directly to the target site, i.e., the periodontal pocket. Also, as these products are typically administered by dental professionals, patient compliance is not an issue.

Administration of microparticles in dry form to the periodontal pocket by use of an apparatus has been disclosed in U.S. Pat. Nos. 5,236,355, 5,366,733 and 5,622,498, all to Brizzolara, et al., and U.S. Pat. No. 6,682,348, to Lawter, et al., the contents each of which are incorporated by reference herein. These patents disclose treating dental diseases by administration of dry microparticles to the periodontal pocket. Microparticles suitable for this purpose may have compositions, as described in U.S. Pat. Nos. 5,000,886, 5,143,661 and 5,500,228, all to Lawter, et al., all three of these patents are incorporated by reference herein, and U.S. Pat. Nos. 5,236,355, 5,366,733 and 5,622,498, all to Brizzolara, et al., and may be produced by the methods disclosed in the aforementioned six U.S. patents.

The apparatus described in the above listed patents deliver microparticles by use of a plunger to push microparticles out of a hollow cannula. The outlet of the cannula is inserted into a periodontal pocket prior to delivery of the microparticles. During administration of microparticles with such a device, there is a tendency to push the cannula outlet against tissue in the bottom of the periodontal pocket while pushing on the plunger. Tissue may block the outlet and increase the force required to push the microparticles out. At high doses of microparticles in a dry powder form, the force may be too large to easily push out the medicament, since the force required to expel a dry powder will increase rapidly with the length of the powder column. This effect may be overcome to some extent by increasing the interior diameter of the tip. However, when it is desired to deliver microparticles to a body cavity of small dimensions such as a periodontal pocket, there are limitations on the diameter of the tip. Thus, there is a need for improved devices for delivering medicaments to periodontal pockets of a human or animal. There is also a need for a device that provides the ability to administer multiple doses of a medicament.

SUMMARY OF THE INVENTION

The present invention is directed to a device for inserting a medicament within a body cavity of a mammal, e.g. the periodontal pocket of a human or animal. The device includes a cartridge for containing medicament, the cartridge including a retractable chamber with an internal surface, an external surface and a lumen defined by the internal surface. Medicament may be disposed within the chamber. The chamber may have a distal tip with a uniform external cross-section sized to fit within the body cavity. The device further includes a substantially stationary member disposed within the lumen of the chamber. The substantially stationary member has a uniform cross-section sized to provide a sliding fit within the lumen to provide for retraction of the retractable chamber about the substantially stationary member upon actuation of the device. The device also includes a means for retracting the retractable chamber while maintaining the substantially stationary member in a substantially stationary position relative to the device and the body cavity. The device also includes means for activating the means for retracting the retractable chamber. The device thus is configured so that the medicament is expelled from the opening of the chamber by retraction of the chamber about the medicament and the substantially stationary member, rather than by forward movement of the substantially stationary member within the chamber to force the medicament from the end of the barrel.

The devices of the present invention are utilized in a method for administering a medicament to body cavity of a mammal, e.g. the periodontal pocket of a human or animal, including: obtaining the medicament containing cartridge and the actuator for dispensing medicaments; attaching the cartridge to the actuator; and pressing the operating lever or trigger of the actuator to retract the retractable chamber while maintaining the substantially stationary member in a substantially stationary position relative to the device and the body cavity so that the medicament is expelled from the opening of the chamber by retraction of the chamber about the medicament and the substantially stationary member.

BRIEF DESCRIPTION OF THE FIGURES

FIG. 3 is an exploded view of a cartridge in accordance with one embodiment of the invention;

FIG. 4 is a cross-sectional side view of the cartridge of FIG. 3 after assembly;

FIG. 6d is a cross-sectional enlarged side view of the distal end of the medicament delivery device shown in FIG. 6a;

FIG. 9a is a partially open side view of a fourth exemplary embodiment of the medicament delivery device according to the present invention;

FIG. 9b is a cross-sectional side view of a fourth embodiment of the medicament delivery device according to the present invention.

FIG. 10a is a perspective view of a fifth embodiment of the medicament delivery device according to the present invention;

FIG. 10b is a partial cross-sectional side view of a fifth embodiment of the medicament delivery device according to the present invention;

FIG. 11a is a partial cross-sectional side view of sixth exemplary embodiment of the medicament delivery device according to the present invention, prior to connection between the cartridge and the actuator;

FIG. 11b is a cross-sectional side view of FIG. 11a, after the connection between the cartridge and the actuator, and prior to delivery of a first dose of the medicament;

FIG. 11e is a cross-sectional side view of FIG. 11d when reset for delivery of a second dose of medicament;

FIG. 11f is a cross-sectional side view of FIG. 11e as delivery of the second dose of medicament is performed;

FIG. 11g is a cross-sectional side view of FIG. 11f after delivery of the second dose of medicament;

FIG. 11h is a cross-sectional side view of FIG. 11g when reset for delivery of a third dose of medicament;

FIG. 11i is a cross-sectional side view of FIG. 11h as delivery of the third dose of medicament is performed;

FIG. 11j is a cross-sectional side view of FIG. 11i after delivery of the third dose of medicament;

FIG. 12a is a partial cross-sectional side view of seventh exemplary embodiment of the medicament delivery device according to the present invention, prior to connection between the cartridge and the actuator;

FIG. 12b is a cross-sectional side view of FIG. 12a, after the connection between the cartridge and the actuator, and prior to delivery of a first dose of the medicament;

DETAILED DESCRIPTION OF THE INVENTION

Figure 1A:
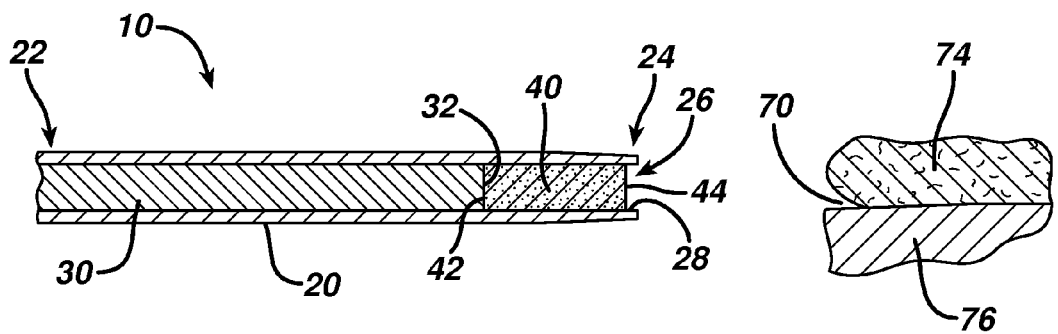
FIG. 1a is a cross-sectional side view of a distal portion of a chamber containing a medicament disposed therein in accordance with one embodiment of the invention, prior to delivery of the medicament into the body of a mammal.
Figure 1B:
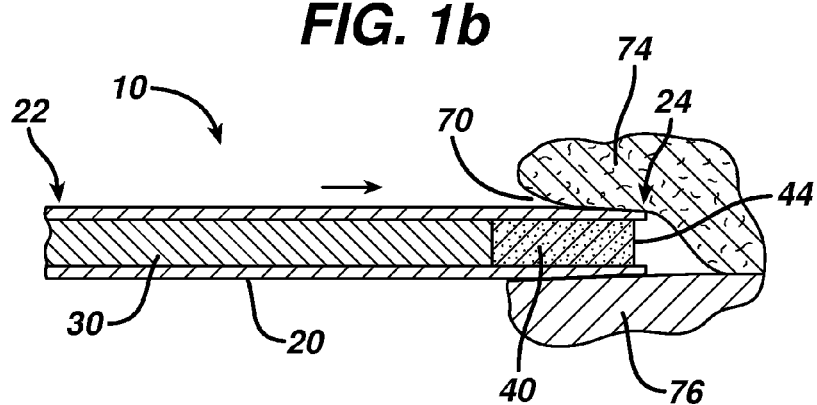
FIG. 1b is a cross-sectional side view of the chamber of FIG. 1a placed at the site of delivery of medicament.
Figure 1C:
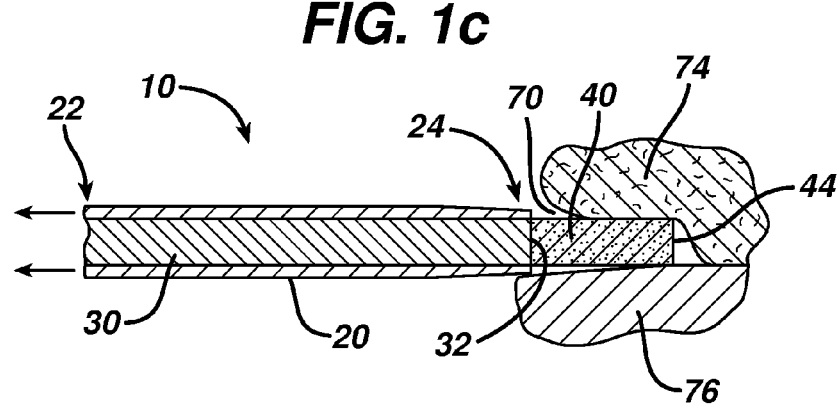
FIG. 1c is a cross-sectional side view of the chamber of FIG. 1b after retraction of the chamber.
Figure 1D:
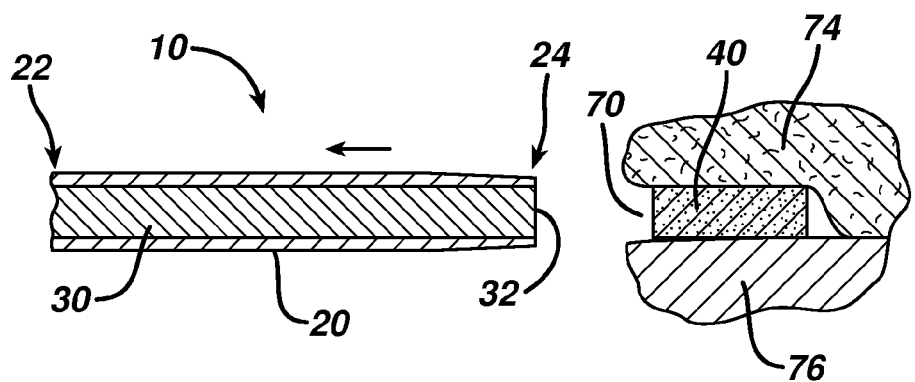
FIG. 1d is a cross-sectional side view of the chamber of FIG. 1c upon removal from the mammal after delivery of medicament to the mammal.

The present invention relates to devices used to administer medicaments into a body cavity of a mammal, e.g. the periodontal pocket of a human or animal. The devices may contain a single dose or multiple doses of medicament, for example in solid powder form, as discussed herein. Such devices include a cartridge for housing a retractable chamber, the retractable chamber for containing medicament, and an actuator for placing the device in operation once the distal portion of the medicament-containing chamber is inserted within the body cavity, thus providing for delivery of the medicament within the body cavity. In certain embodiments, devices may include a sealing means, such as a gasket, to prevent backflow of the medicament between the internal surface of the chamber and the substantially stationary member upon operation of the device. Devices of the present invention are particularly useful and advantageous for administration of a medicament to the periodontal pocket of a mammal for treatment of periodontitis.

In practice, the medicament is placed within the retractable chamber and the chamber then is placed within the cartridge. The cartridge then is connected to the actuator in operational engagement. The distal tip of the retractable chamber extending beyond the distal end of the cartridge is placed within the body cavity at the desired site of delivery of medicament. The actuator then is employed in cooperation with the cartridge to retract the chamber away from the delivery site in a direction towards the actuator. Upon retraction of the chamber, the substantially stationary member (hereinafter SSM) within the chamber that is in contact with the medicament maintains the medicament at the delivery site, thus leaving the medicament that was disposed within the tip of the chamber in the body cavity at the desired delivery site. Cartridges used in devices of the present invention are replaceable and may include a single or multiple doses of medicament contained therein. Multiple doses are advantageous, as a single cartridge may be employed to deliver medicament to multiple delivery sites prior to replacement. This is particularly advantageous for administration of a medicament to the periodontal pocket of a human for treatment of periodontitis, where delivery at multiple sites often is required and discomfort of the patient may be a substantial issue. The chamber used in devices according to the present invention, may be in the form of a retractable, cannulated barrel, where the barrel has an outer surface and an inner surface forming the body of the barrel. The lumen of the barrel then is defined by the configuration of the inner surface. Devices also include an SSM disposed within the lumen of the barrel. The respective cross-sections of the lumen of the barrel and the SSM are sized to provide a slidable fit between the inner surface of the barrel and the outer surface of the SSM. By slidable fit, it is meant that co-axial movement of the barrel relative to the SSM may be accomplished without use of excessive force, while maintaining a spatial relationship between the inner surface of the barrel and the outer surface of the SSM, so as to avoid unnecessary movement or "wobbling" of the SSM within the barrel. Upon activation of the device, the barrel slides about the SSM in a lateral direction away from the body cavity, towards the distal end of the device, while the SSM itself remains substantially stationary. By substantially stationary, it is meant that, upon activation of the device to deliver the medicament to the body cavity, the SSM remains in a substantially stationary position in relation to the device itself and to the point within the body cavity at which the medicament is being delivered. While some movement of the SSM relative to the insertion site might occur, any such movement should not be sufficient to cause tissue to block the outlet of the barrel or to appreciably increase the force required to deliver the medicament at the site of insertion. This is particularly advantageous where the medicament may be in the form of a dry solid powder, such as a dry microparticle powder or microspheres.

Typically, but optionally, additives, such as diluents, carriers, excipients, stabilizers or the like may be included in the formulation.

In one embodiment, medicaments may be in the form of a particulate composition, such as a dry microparticle powder composition in a sufficient treatment quantity. For example, the composition can be ARESTIN® minocycline Hydrochloride (HCl) microspheres, available from OraPharma, Inc., Warminster, Pa., for example, in a 1 mg dosage, or those compositions as disclosed in U.S. Pat. Nos. 5,000,886, 5,143,661, 5,236,355, 5,366,733, 5,500,228, and 5,622,498, all six disclosures of which are incorporated by reference in their entirety herein. These compositions may comprise matrices of biocompatible and biodegradable polymers, in accordance with the disclosure of U.S. Pat. Nos. 5,236,355, 5,366,733, 5,500,228, and 5,622,498.

For example, dry microparticle compositions may include therapeutic agents, such as antibacterials, antibiotics, antifungal agents, anti-inflammatory agents, immunosuppressive agents, immunostimulatory agents, dentinal desensitizers, odor masking agents, immune reagents, anesthetics, antiseptics, nutritional agents, antioxidants, lipopolysaccharide complexing agents, peroxides, growth factors, or mixtures thereof. The therapeutic agent could also have antibiotic activity.

Exemplary therapeutic agents may be antibiotics such as tetracycline, a pharmaceutically acceptable salt of a tetracycline, hydrates of a tetracycline and hydrates of a pharmaceutically acceptable salt of a tetracycline. The tetracyclines may be doxycycline, a pharmaceutically acceptable salt of doxycycline, hydrates of doxycycline and hydrates of a pharmaceutically acceptable salt of doxycycline. Also, the tetracycline may be minocycline, a pharmaceutically acceptable salt of minocycline, hydrates of minocycline and hydrates of a pharmaceutically acceptable salt of minocycline.

These exemplary therapeutic agents may be present in the form of particles within the medicament. They can typically range from about 0.00001 to about 50 parts by weight per 100 parts by weight of the particles or from about 1 to about 50 parts by weight per 100 parts by weight of the particles, or more particularly from about 4 to about 40 parts by weight per 100 parts by weight of the particles.

Alternatively, the therapeutic agent may be present in the medicament as a liquid or gas.

Polymers for the aforementioned matrices may include polyglycolide, poly(1-lactide), poly(dl)lactide, poly(glycolide-co-lactide), poly (glycolide-co-lactide), poly(hydroxybutyric acid, poly(orthoesters), poly(p-dioxanone) and mixtures thereof. The polymers can also be block copolymers of polyglycolide, trimethylene carbonate and polyethylene oxide or polyoxyethylene-polyoxypropylene copolymers. The polymers can also be biopolymers and their derivatives including cellulose, cellulose derivatives (oxidized regenerated cellulose), starch, gelatin, chitosan, and hyaluronan. These polymers may also be such that they become tacky upon contact with water.

The aforementioned particles of particulate compositions including therapeutic agents may, for example, have particles with diameters ranging from about 0.1 to about 1,000 microns, or from about 10 to about 200 microns, or from about 20 to about 120 microns.

While the figures are presented as exemplary embodiments of the inventions, they are not intended to limit the scope of the invention or the claims appended hereto. Use of the same reference symbols in different figures indicates similar or identical items.

One embodiment of the present invention is shown in FIG. 1a. FIG. 1a is a cross-sectional side view of a distal portion of retractable chamber 10, in the form of retractable barrel 20 for holding a dose of medicament 40. Medicament 40 is disposed in the lumen defined by the internal surface 28 of barrel 20. Substantially stationary member (SSM) 30 is disposed within barrel 20. Barrel 20 is cannulated to allow passage co-axially about SSM 30, and has proximal 22 and distal 24 ends, as well as a distal opening 26. SSM 30 is shown to have distal face 32. Medicament 40 is located in cannulated barrel 20, and has proximal 42 and distal 44 interfaces. The proximal interface 42 is in contact with distal face 32 of SSM 30. The cross-sectional dimensions, e.g. the diameter, of the lumen of barrel 20 relative to the cross-sectional dimension of SSM 30 is such that barrel 20 may move co-axially about SSM 30 in a sliding fit without medicament 40 leaking between SSM 30 and inner surface 28 of barrel 20, and provide for retraction of barrel 20 around SSM 30. This is particularly applicable to medicaments in powder form. The cross-sectional shape of SSM 30 and lumen of barrel 20 may be hexagonal, octagonal, elliptical or any other shape, with a circular cross-sectional shape being preferred. In one embodiment, SSM 30 has a bell shaped feature (not shown) on the both ends to create seals with barrel 20.

Suitable materials from which barrel 20 and SSM 30 may be formed include glasses, non-corrodible metals, synthetic resins such as plastics, and the like. These materials may be used alone or in combination. If the device components are made of glasses, non-corrodible metals, or sterilizable synthetic resins, they may be used repeatedly by performing sterilization. Preferably, barrel 20 and SSM 30 are formed from synthetic resins such as plastics. Plastics may include polyethylene, polypropylene, and polycarbonate.

FIGS. 1a to 1d show the steps in the delivery of medicament 40 to a delivery site 70 of a patient. In this embodiment, delivery site 70 is in the form of a pocket between a first tissue 74, for example a gum, and a second tissue 76, for example a tooth, such as a periodontal pocket in a mammal. FIG. 1a show chamber 10 prior to delivery, where proximal interface 42 of medicament 40 is in contact with distal face 32 of SSM 30. In the first step, chamber 10 is placed at delivery site 70 by inserting distal end 24 in the direction of the arrow in FIG. 1b into site 70. Now, SSM 30 is held substantially stationary while barrel 20 is retracted about SSM 30 in the direction of the arrow in FIG. 1c. Medicament 40 is delivered from the barrel distal opening 26 by retracting barrel 20. Medicament 40 is fully administered when distal end 24 of barrel 20 reaches distal face 32 of SSM 30. Finally, chamber 10 is removed from delivery site 70 (see FIG. 1d) in a distal to proximal direction, leaving medicament 40 at delivery site 70.

Figure 2A:
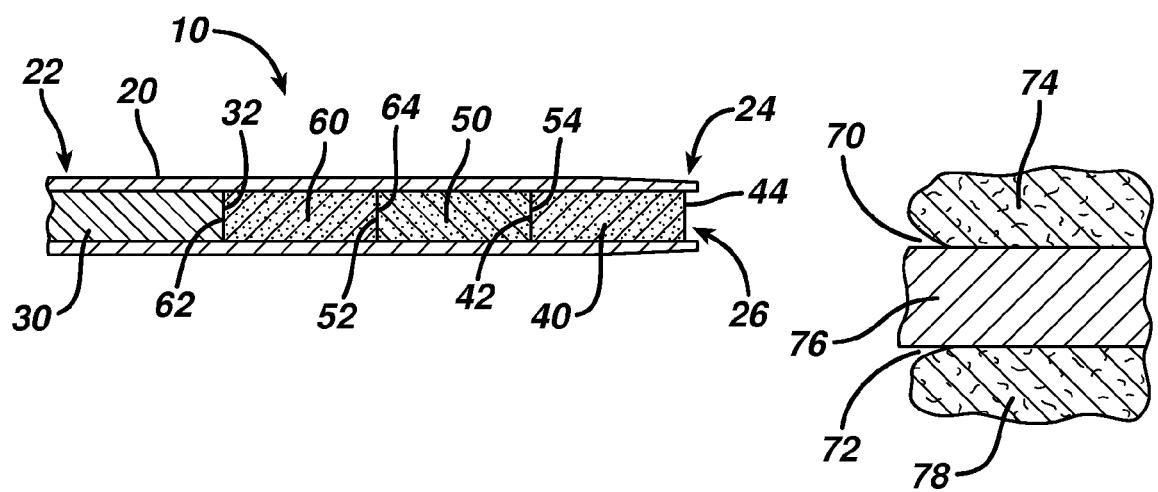
FIG. 2a is a cross-sectional side view of a distal portion of a chamber containing multiple doses of a medicament disposed therein in accordance with one embodiment of the invention, prior to delivery of the medicament into the body of a mammal.
Figure 2B:
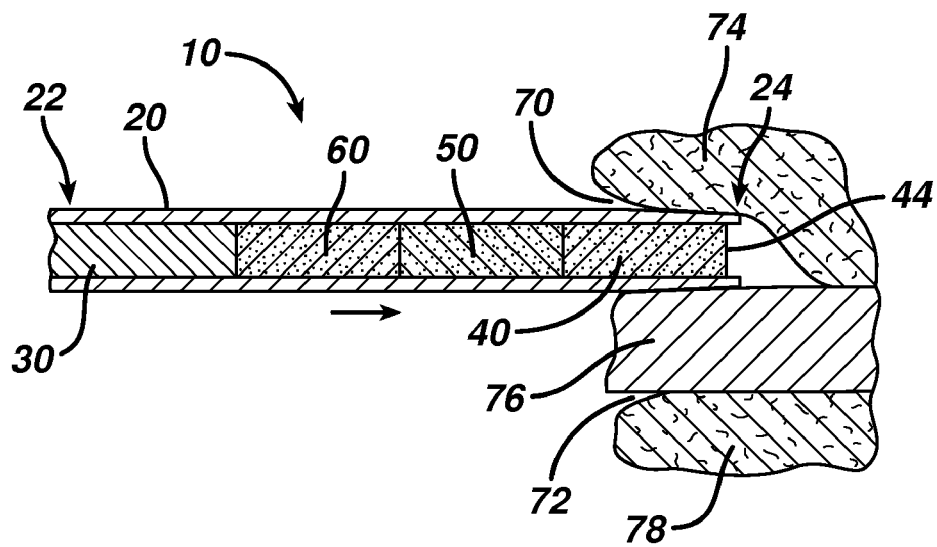
FIG. 2b is a cross-sectional side view of the chamber of FIG. 2a placed at the site of delivery of the first dose of medicament.
Figure 2C:
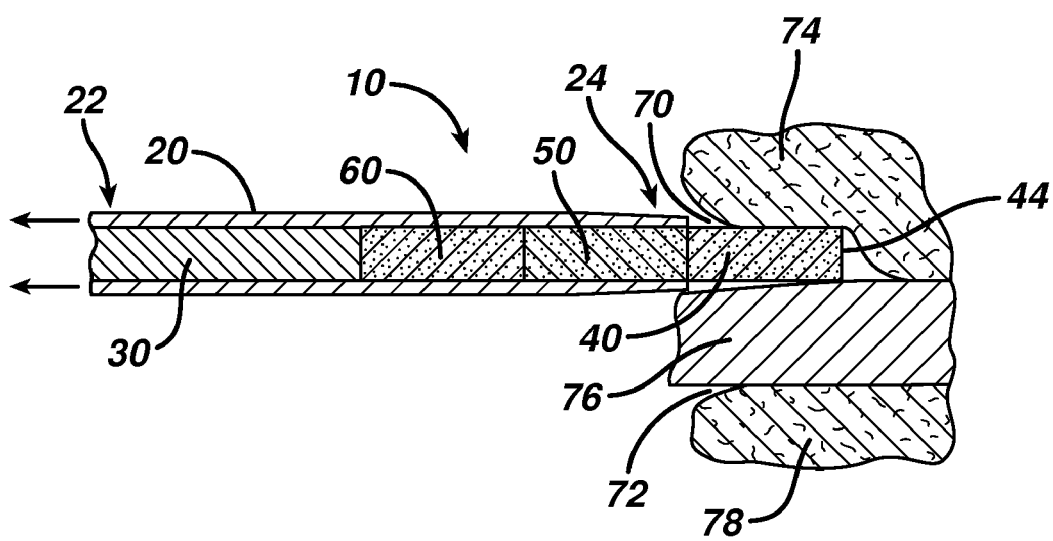
FIG. 2c is a cross-sectional side view of the chamber of FIG. 2b after retraction of the chamber.
Figure 2D:
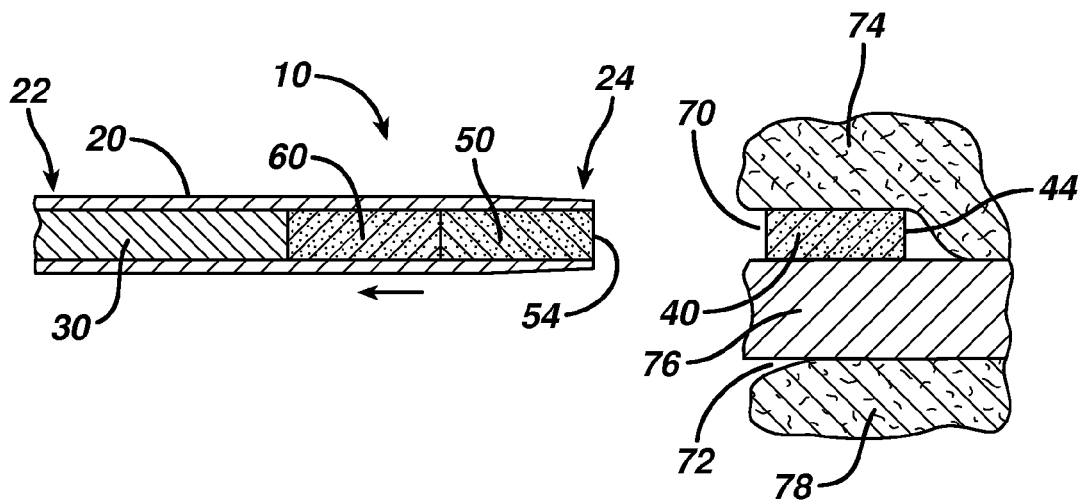
FIG. 2d is a cross-sectional side view of the chamber of FIG. 2c upon removal from the mammal after delivery of the first dose of medicament to the mammal.
Figure 2E:
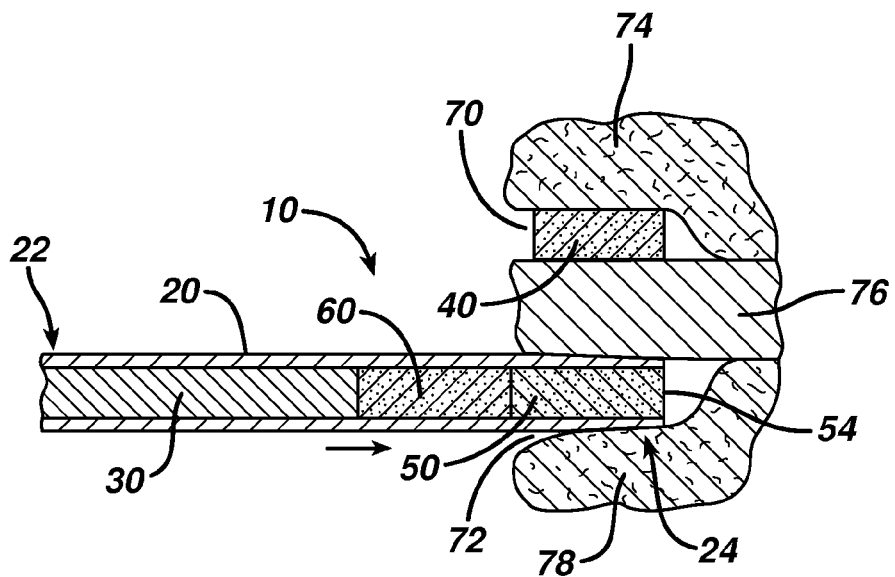
FIG. 2e is a cross-sectional side view of the chamber of FIG. 2d placed at the site of delivery of the second dose of medicament.
Figure 2F:
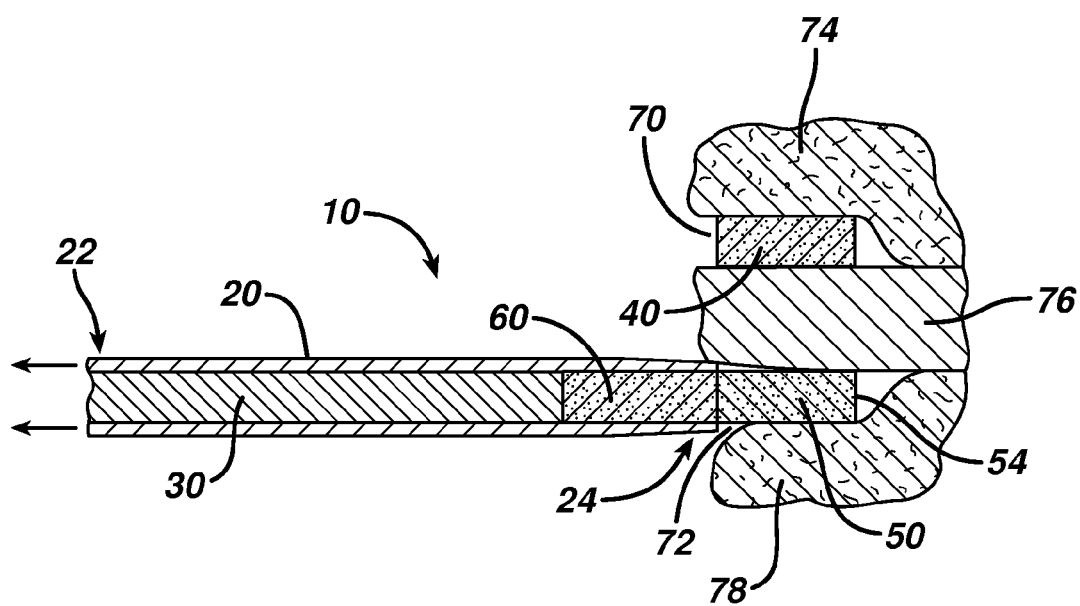
FIG. 2f is a cross-sectional side view of the chamber of FIG. 2e after retraction of the chamber.

An alternative embodiment of the present invention is shown in FIG. 2a. FIG. 2a is similar to FIG. 1a, except that multiple doses 40, 50, and 60 are located in the lumen (defined by the internal surface of barrel 20) of retractable barrel 20.

Additional doses of medicament may be disposed within barrel 20, for example four or more doses. Second medicament dose 50 has proximal 52 and distal 54 interfaces. Third medicament dose 60 has proximal 62 and distal 64 interfaces. Second and third medicament doses 50 and 60 may be comprised of the same formulation as first medicament dose 40, or of a different formulation than first medicament dose 40. The embodiment as shown in FIG. 2a allows for the delivery of multiple doses of medicament.

FIGS. 2a to 2f show the steps in the delivery of medicament doses 40 and 50 to first delivery site 70 and second delivery site 72, respectively. In this embodiment, first delivery site 70 is in the form of a pocket between a first tissue 74 and a second tissue 76, while second delivery site 72 is in the form of a pocket between a second tissue 76 and a third tissue 78. First delivery site 70 and second delivery site 72 may be, for example periodontal pockets in a mammal. FIG. 2a shows chamber 10 prior to delivery, where proximal interface 42 of first medicament dose 40 is in contact with distal interface 54 of second medicament dose 50 and proximal face 52 of second medicament dose 50 is in contact with distal face 64 of third medicament dose 60. In the first step, chamber 10 is placed at delivery site 70 (see FIG. 2b). Now, SSM 30 is held substantially stationary while barrel 20 is retracted in the direction of the arrow in FIG. 2c. First medicament dose 40 is delivered from the barrel distal opening 26 by retracting barrel 20. First medicament dose 40 is fully administered when distal face 54 of second medicament dose 50 reaches distal end 24 of barrel 20. Next, chamber 10 is removed from delivery site 70 (see FIG. 2d) from a distal to proximal direction, leaving first medicament dose 40 at delivery site 70. Next, chamber 10 is aligned for next delivery and then placed at delivery site 72 (see FIG. 2e). Now, SSM 30 is held substantially stationary while barrel 20 is retracted in the direction of the arrow in FIG. 2f. Second medicament dose 50 is delivered from the barrel distal opening 26 by retracting barrel 20. Second medicament dose 50 is fully administered when proximal face 52 of second medicament dose 50 reaches distal end 24 of barrel 20. Next, chamber 10 is removed from delivery site 72 from a distal to proximal direction, leaving second medicament dose 50 at delivery site 72. This process may be repeated depending on the desired number of doses of medicament to be administered.

FIG. 3 is an exploded view of a cartridge in accordance with one embodiment of the invention. Such cartridges will include a housing having disposed therein a retractable chamber for containing medicament, a substantially stationary member (SSM) disposed within the retractable chamber and means for retracting the chamber. Components of cartridge 100 include housing 110, retractable chamber in the form of barrel 130, cartridge spring 150 disposed about barrel 130 for enabling barrel 130 to retract upon actuation of the device, and substantially stationary member (SSM) 160 disposed within barrel 130. Optionally, cartridge 100 may have retaining cap 170 to protect the medicament from contamination. All components of cartridge 100 may be made from stainless steel or known plastics, or, optionally, any material that can be sterilized. Plastics may include polyethylene, polypropylene, and polycarbonate. The retaining cap may be made of an elastic material, such as rubber, thermoplastic elastomer or silicone rubber. Barrel 130 may optionally contain a lubricant to facilitate delivery of the medicament. The lubricant may be applied to the surfaces of the barrel or may be included as a slip agent in a resin used to manufacture the part by injection molding. Suitable slip agents include oleamide.

A cross-sectional side view of cartridge 100 useful in the present invention is shown in FIG. 4. As shown, cartridge 100 includes housing 110, retractable chamber in the form of barrel 130 disposed within housing 110, spring 150 disposed about barrel 130 for retracting barrel 130 upon actuation of the device and SSM 160 disposed within barrel 130. Barrel 130 is sized to fit slidably within housing 110. Barrel 130 includes proximal end 132 and distal end 134, and barrel extension 135. Medicament (not shown in FIGS. 3 and 4) is located in the cannulation or lumen 136 of barrel 130. Distal end 134 of barrel 130 includes distal tip 138 and distal opening 142. When the cartridge is in loaded engagement with an actuator, i.e. ready to dispense medicament, spring 150 biases barrel 130 towards proximal end 114 of housing 110 to provide a retracting motion for barrel 130 when actuated.

Housing 110 may be made from the same materials as barrel 130. Housing 110 includes proximal end 112 and tapered distal end 114. Though not shown, distal end 114 of housing 110 may have a bend of approximately 50 degrees to facilitate entry of distal tip 138 of barrel 130 into the body cavity. In such cases, barrel 130 will be made from a plastic and will be flexible so as to traverse the housing. Housing 110 may include means for finger gripping such as fins 116, which enable the barrel to be rotated. Housing 110 may contain means for retaining cap 170 to protect the medicament from contamination, such as snap ring 118 located on distal end 114. Housing 110 may include means for limiting the motion of barrel 130, such as slots 122 that align with barrel extension 135. Proximal end 112 of housing 110 may include means for attaching cartridge 100 to an actuator (not shown), such as fingers 124 with flanges 126, which engage an undercut on the tip of the actuator.

Figure 5A:
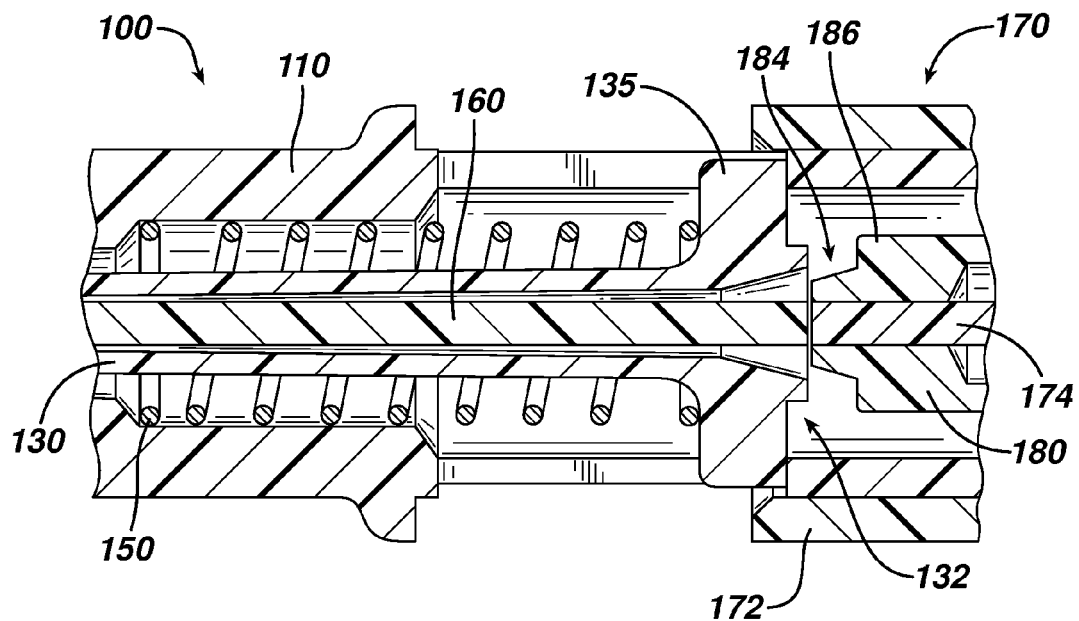
FIG. 5a is a cross-sectional side view of the proximal portion of a cartridge and the distal portion of an actuator according to one embodiment of the invention prior to connection.
Figure 5B:
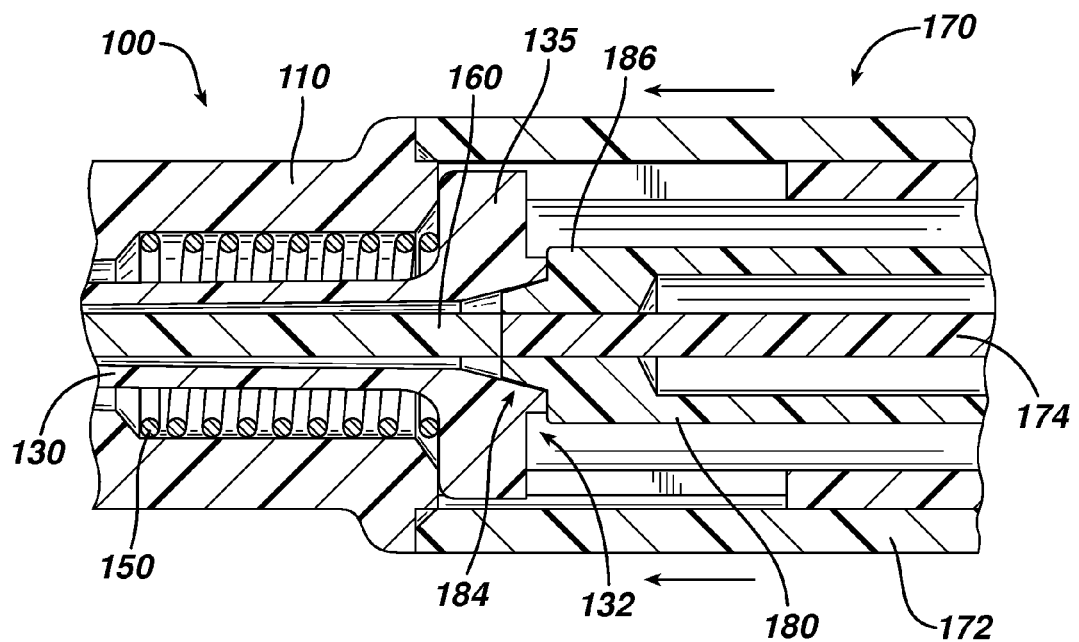
FIG. 5b is a cross-sectional side view of FIG. 5a after connection.

Dispensing medicament from cartridge 100 of the present invention is effected by an actuator used in operational engagement with the cartridge. FIGS. 5a and 5b are cross-sectional side views of a proximal portion of cartridge 100 and a distal portion of actuator 170 shown prior to and after connection of the two parts. The figures show a proximal portion of cartridge 100, including housing 110, retractable chamber in the form of barrel 130, retracting spring 150 disposed about barrel 130, and SSM 160 disposed within barrel 130. Barrel extension 135 and proximal end 132 of barrel are also shown. The figures also show a portion of actuator 170, including tube tip 172 and inner sleeve 180. Inner sleeve shoulder 186 and inner sleeve distal end 184 are also shown.

As shown in FIG. 5a, proximal end 132 of barrel 130 is aligned with inner sleeve distal end 184 prior to connection between cartridge 100 and actuator 170. The opening at proximal end 132 of barrel 130 and inner sleeve distal end 184 are tapered to allow a male to female fit of inner sleeve 180 to barrel 130.

To complete the connection of actuator 170 to cartridge 100, actuator 170 may be moved distally (in the direction of the arrow in FIG. 5b) while cartridge 100 is kept substantially stationary. The actuator and cartridge may also be brought together by holding the actuator substantially stationary while moving the cartridge, or by bringing the two together in relative motion. After connection between cartridge 100 and actuator 170, proximal end 132 of barrel 130 is aligned with inner sleeve shoulder 186. During the actuator-to-cartridge connection, SSM 160 moves distally (in the direction of the arrow in FIG. 5b) within barrel 130, compacting the medicament (not shown) located in the lumen at the distal end of barrel 130. Compacting may be necessary, depending on the properties of the medicament, in those cases where delivery of multiple substantially equal doses is important. For example, powders may benefit from this compacting, ensuring a consistent powder density from dose to dose.

Figure 6A:
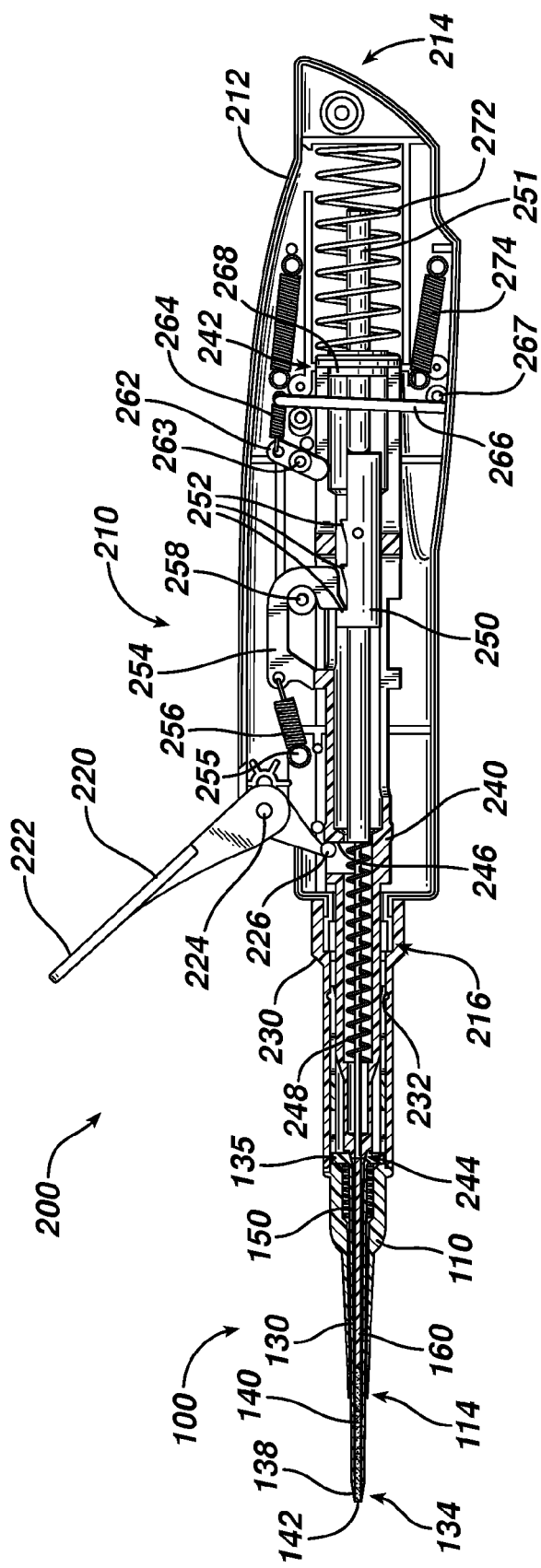
FIG. 6a is a partial cross-sectional side view of a device according to the present invention, prior to delivery of a first dose of the medicament.

FIG. 6a is a partial cross-sectional side view of an exemplary embodiment of the medicament delivery device according to the present invention. The figure shows device 200 comprised of cartridge 100 and a first embodiment actuator 210, which provides means for activating the means for retracting retractable barrel 130. The cartridge is as shown in FIGS. 3-5b and described previously herein. Actuator 210 comprises an outer handle case 212. The handle case, as well as all other components of actuator 210, may be made from stainless steel, but could be made of any material that can be sterilized. Actuator 210 may be sterilized between use on different patients to avoid disease transmission. Handle case 212 may be formed as two pieces that can be affixed together, e.g. by a screw, and is designed to provide means for gripping the actuator. Handle case 212 has a proximal portion 214 for gripping and a distal portion 216 having means for connecting to cartridge 100. One suitable means for connecting the cartridge with the actuator is a tube tip 230, which is positioned at the distal portion 216 of the actuator 210. Tube tip 230 may be connected to the handle by threading it onto handle case 212. The tube tip may have an undercut 232 on its inner surface to retain cartridge 100.

In this first embodiment, actuator 210 converts a rotational motion to linear motion. Actuator 210 has an operating lever 220 located on the upper surface at distal portion 216 of handle case 212. Operating lever 220 has a finger-manipulating portion 222, and pin 224 and lobe 226 for creating linear motion from rotational motion. Within handle case 212 is a cannulated inner sleeve 240 having a proximal portion 242, a tapered distal portion 244 for interfacing inner sleeve 240 with barrel extension 135 of barrel 130, and a vertical wall with flat surface 246 for engaging lobe 226 of operating lever 220.

Within the cannulation of inner sleeve 240 is inner sleeve spring 248, and inner ratchet 250 with at least one step 252 (three steps shown in FIG. 6a). The inner sleeve contains a recess for connecting a ratchet pawl 254 to the inner sleeve. The inner sleeve also contains a slot for maintaining the orientation between the pawl and the ratchet 250. A pawl spring 256 connects ratchet pawl 254 to a pin 255 in handle case 212. Pawl spring 256 biases ratchet pawl 254 to remain engaged with first ratchet step 252. The axial movement of ratchet pawl 254 is limited by pawl pin 258. The distal end of inner ratchet 250 is engaged with the proximal end of SSM 160. Inner sleeve spring 248 is located within the cannulation of inner sleeve 240, surrounding distal portion of inner ratchet 250 and biasing the inner ratchet towards the proximal end 214 of handle case 212.

The proximal portion 251 of ratchet 250 is placed in a clutch 266. The clutch 266 pivots about a pin 267 located on the handle case 212 to create an immobilized condition, which controls the motion of the ratchet only. A clutch rotational lever 262 rotates around a pin 263 mounted in handle case 212. The clutch rotational lever is connected to the clutch 266 via a spring 264, and controls the immobilized condition of clutch 266. The proximal portion 242 of inner sleeve 240 has a stop washer 268 for engaging a main return spring 272. Main return spring 272 is between stop washer 268 and proximal end 214 of handle case 212 and biases inner sleeve 240 towards distal end 216 of handle case 212.

Figure 6B:
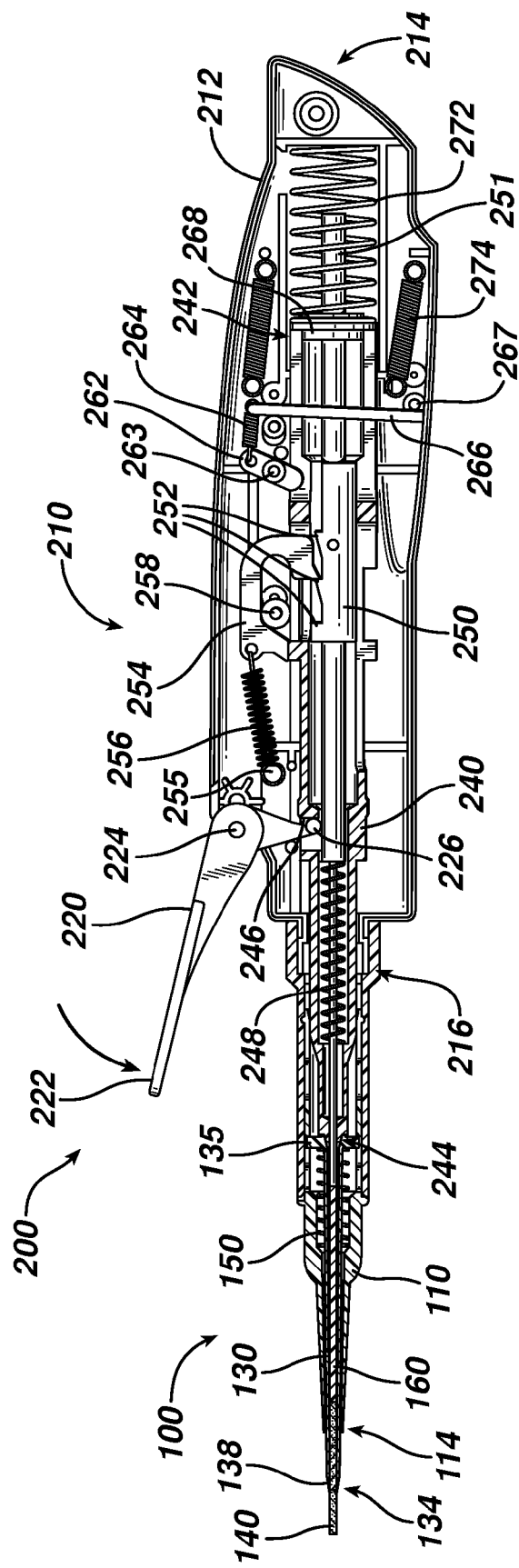
FIG. 6b is a cross-sectional side view of FIG. 6a after delivery of the first dose of medicament.
Figure 6C:
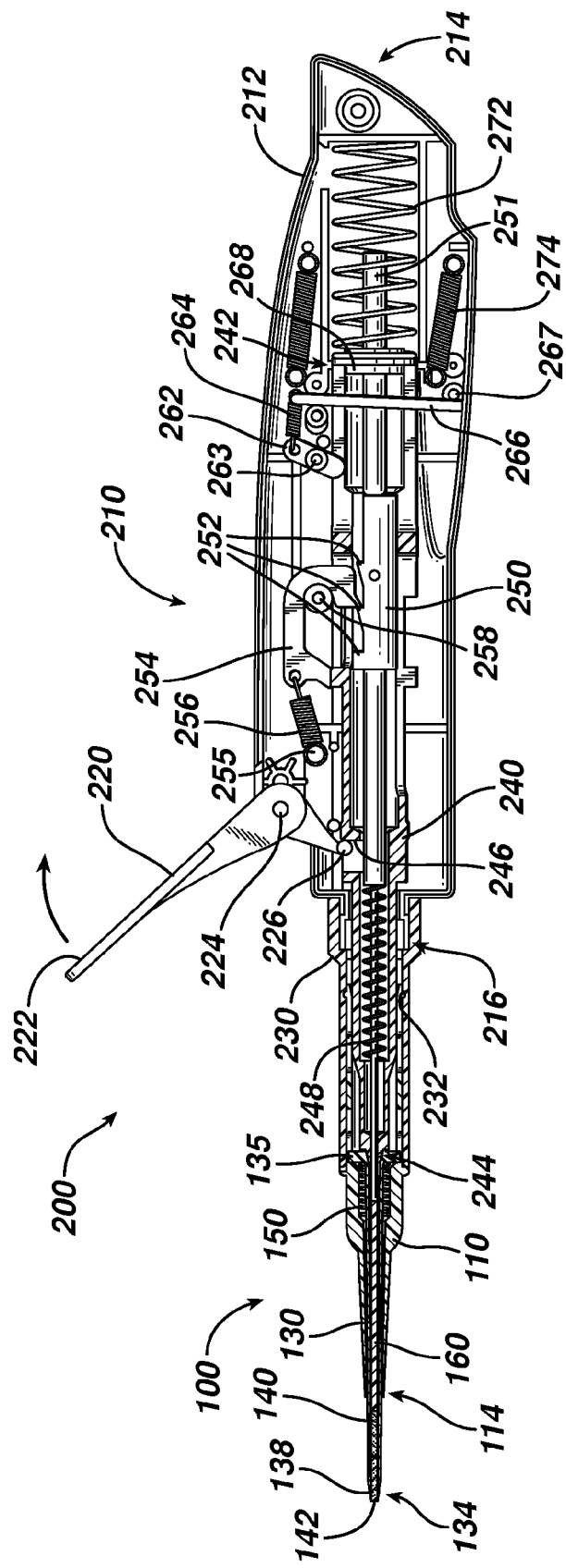
FIG. 6c is a cross-sectional side view of FIG. 6b when reset for delivery of a second dose of medicament.
Figure 6D:
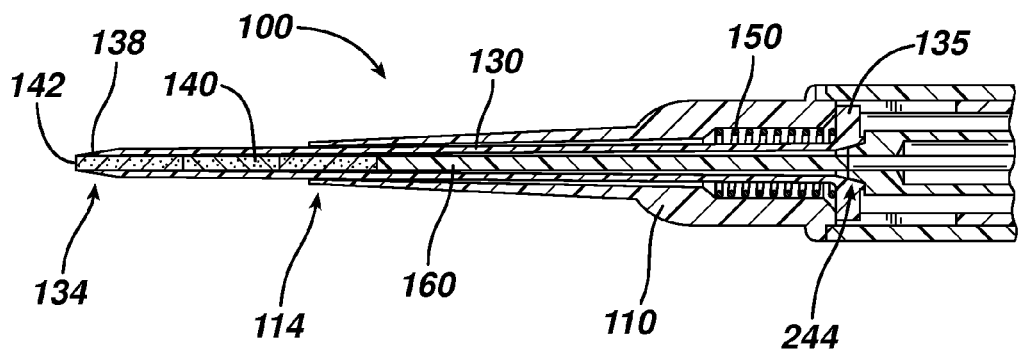
Figure 6E:
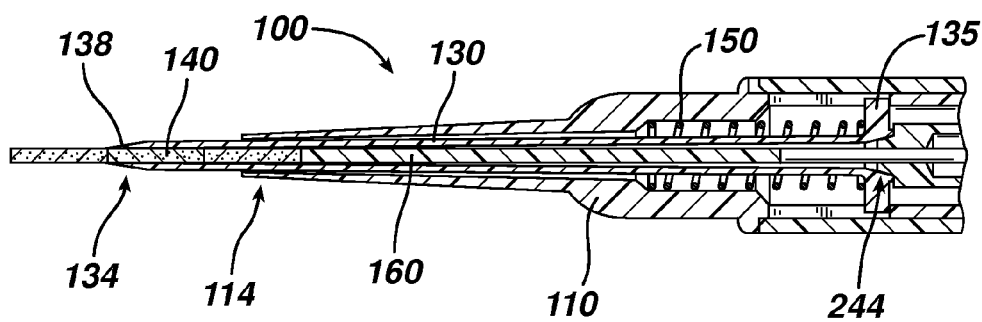
FIG. 6e is a cross-sectional enlarged side view of the distal end of the medicament delivery device shown in FIG. 6b.
Figure 6F:
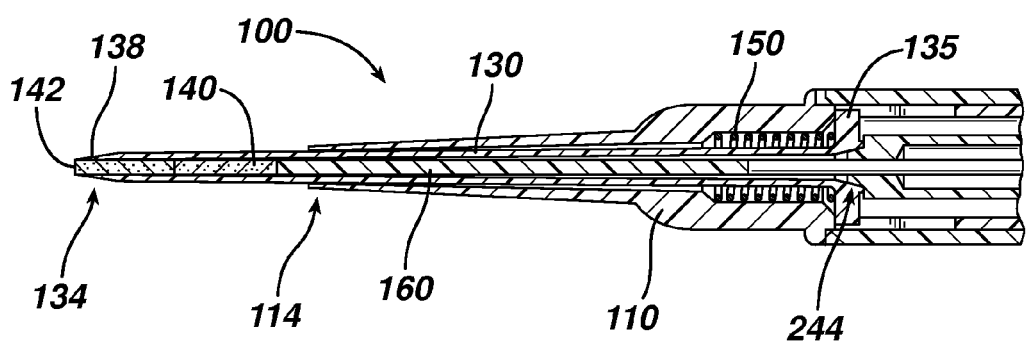
FIG. 6f is a cross-sectional enlarged side view of the distal end of the medicament delivery device shown in FIG. 6c.

FIGS. 6a and 6d show medicament delivery device 200 according to the present invention, prior to delivery of a first dose of the medicament. At this point, clutch 266 is in the immobilized condition, preventing the movement of ratchet 250. A dose of medicament 140 is delivered by pressing down the lever 220 in the direction of the arrow in FIG. 6b. The rotary movement of lever 220 around pin 224 converts to a linear rearward (distal to proximal) motion of inner sleeve 240 via cam action. As mentioned earlier, proximal end 132 of barrel 130 is aligned with inner sleeve shoulder 186 (see FIG. 5b). Cartridge spring 150 biases barrel 130 towards proximal end 132 to provide a distal to proximal (rearward) motion for barrel 130 when inner sleeve 240 moves towards proximal end 214 of handle case 212. At this point ratchet 250, which is engaged with the proximal end of substantially stationary member (SSM) 160, is in the immobilized condition, so ratchet 250 and SSM 160 remain in a relative stationary position with respect to barrel 130 as barrel 130 moves towards proximal end 214 of handle case 212. The retracting motion of barrel 130 releases medicament 140 from distal opening 142 of barrel 130, delivering the medicament to the delivery site as shown in FIG. 6e.

Upon rearward motion (distal to proximal) of the inner sleeve, ratchet pawl 254 is lifted by pawl pin 258 to release pawl 254 from first ratchet tooth 252, and move it to the second ratchet tooth 252. The axial movement of ratchet pawl 254 is then limited by pawl pin 258. Pawl spring 256 is now extended, and biases ratchet pawl 254 to remain engaged with second ratchet step 252. The motion of inner sleeve 240 also rotates clutch rotational lever 262, pulling clutch 266 to the proximal direction to release the immobilized condition. Inner sleeve spring 248 and main return spring 272 are now compressed.

Once medicament dose has been delivered, medicament delivery device 200 may be reset to prepare for next medicament delivery. Device 200 is reset by allowing lever 220 to move in the direction of the arrow in FIG. 6c. Inner sleeve 240 moves towards distal end 216 of handle case 212 due to the force exerted by the relaxation of main return spring 272. Since ratchet 250, which is engaged with the proximal end of SSM 160, is no longer in the immobilized condition, ratchet 250 and SSM 160 move with inner sleeve 240 towards distal end 216 of handle case 212. As a result, distal end 134 of barrel 130 moves distally from distal end 114 of housing 110. Ratchet pawl 254 returns to its starting position, its axial movement limited by pawl pin 258. Pawl spring 256 also relaxes to its starting position. Device 200 is now reset for delivery of next dose of medicament.

Figure 7A:
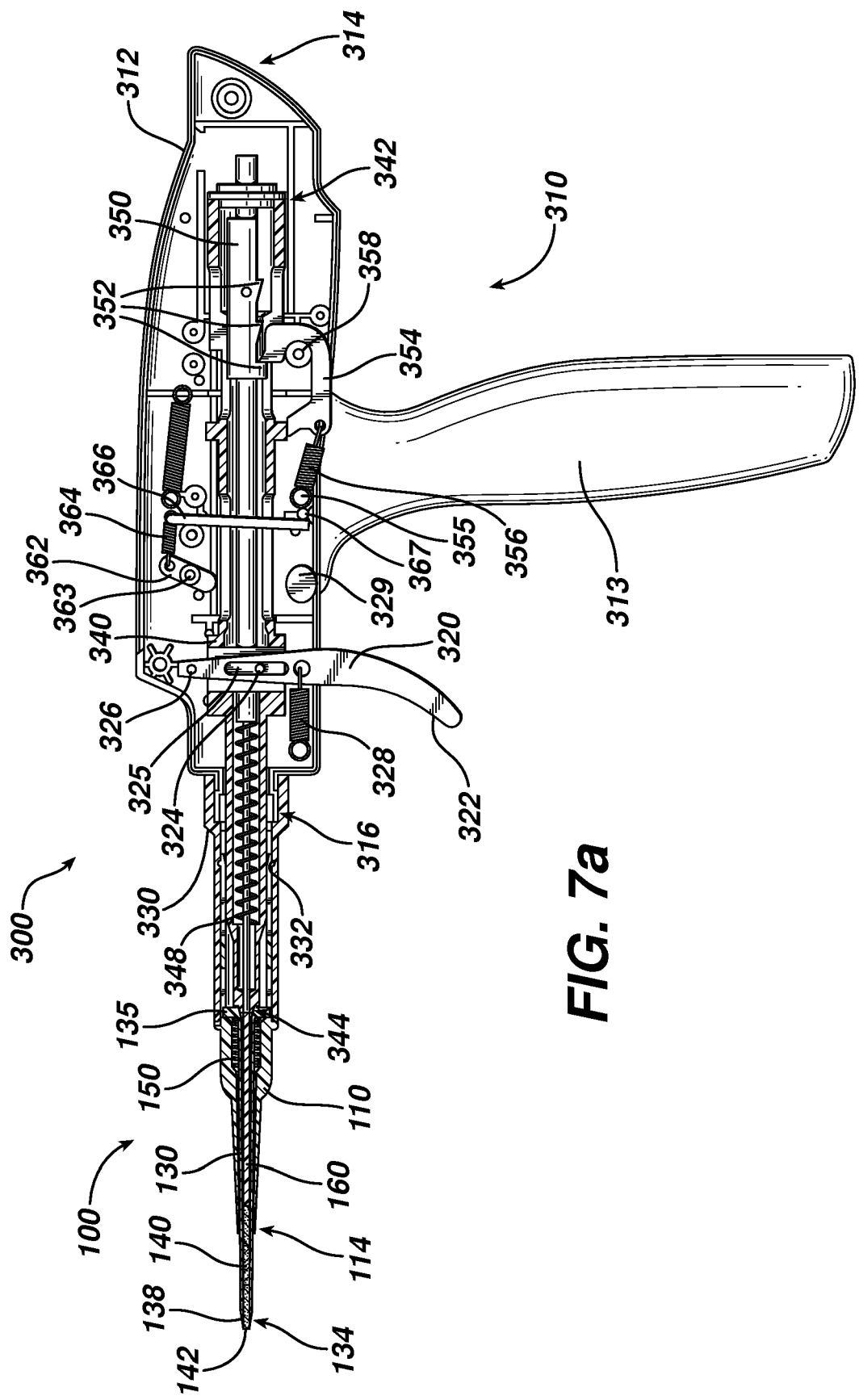
FIG. 7a is a partial cross-sectional side view of a second exemplary embodiment of the medicament delivery device according to the present invention, prior to delivery of a first dose of the medicament.

FIG. 7a is a partial cross-sectional side view of a second exemplary embodiment of the medicament delivery device according to the present invention. The figure shows device 300 comprised of cartridge 100 (as shown in FIG. 4) and second embodiment actuator 310, which provides means for activating the means for retracting retractable barrel 30.

Actuator 310 is made with a handle case 312 and handle 313. All components of actuator 310 may be made from stainless steel, but could be made of any material that can be sterilized. Handle case and handle may be formed as two pieces that can be screwed together. Handle case 312 has a proximal portion 314 and a distal portion 316 having means for attaching cartridge 100. One suitable means for attaching the cartridge is a tube tip 330, which is positioned at the distal portion 316 of the actuator device and may be attached to the handle by threading it onto handle case 312. The tube tip may have an undercut 332 on its inner surface to retain cartridge 100.

In this second embodiment, actuator 310 converts a rotational motion to linear motion. Actuator 310 has a trigger 320 located on the bottom surface near distal portion 316 of handle case 312. Trigger 320 has a finger manipulating portion 322, connection pin 324 located in trigger slot 325, rotation pin 326 fixing trigger to handle case 312, trigger spring 328, which biases trigger towards distal portion 316 of handle case 312, and trigger stop 329. Within handle case 312 is a cannulated inner sleeve 340 having a proximal portion 342, a tapered distal portion 344 for interfacing inner sleeve 340 with barrel extension 135 of barrel 130. Trigger 320 is engaged with inner sleeve 340 via connection pin 324.

Within the cannulation of inner sleeve 340 is inner sleeve spring 348, and inner ratchet 350 with at least one step 352 (three steps shown in FIG. 7a). The inner sleeve contains a recess for connecting a ratchet pawl 354 to the inner sleeve. The inner sleeve also contains a slot for maintaining the orientation between the pawl and the ratchet via a pin. A pawl spring 356 connects ratchet pawl 354 to a pin 355 in handle case 312. Pawl spring 356 biases ratchet pawl 354 to remain engaged with first ratchet step 352. The axial movement of ratchet pawl 354 is limited by pawl pin 358. The distal end of inner ratchet 350 is engaged with the proximal end of substantially stationary member (SSM) 160. Inner sleeve spring 348 is located within the cannulation of inner sleeve 340, surrounding distal portion of inner ratchet 350 and biasing the inner ratchet towards the proximal end 314 of handle case 312.

The central portion of the ratchet is placed in a clutch 366. The clutch 366 pivots about a pin 367 located on the handle case 312 to create an immobilized condition, which controls the motion of the ratchet only. A clutch rotational lever 362 rotates around a pin 363 mounted in handle case 312. The clutch rotational lever is connected to the clutch 366 via a spring 364, and controls the immobilized condition of clutch 366.

Figure 7B:
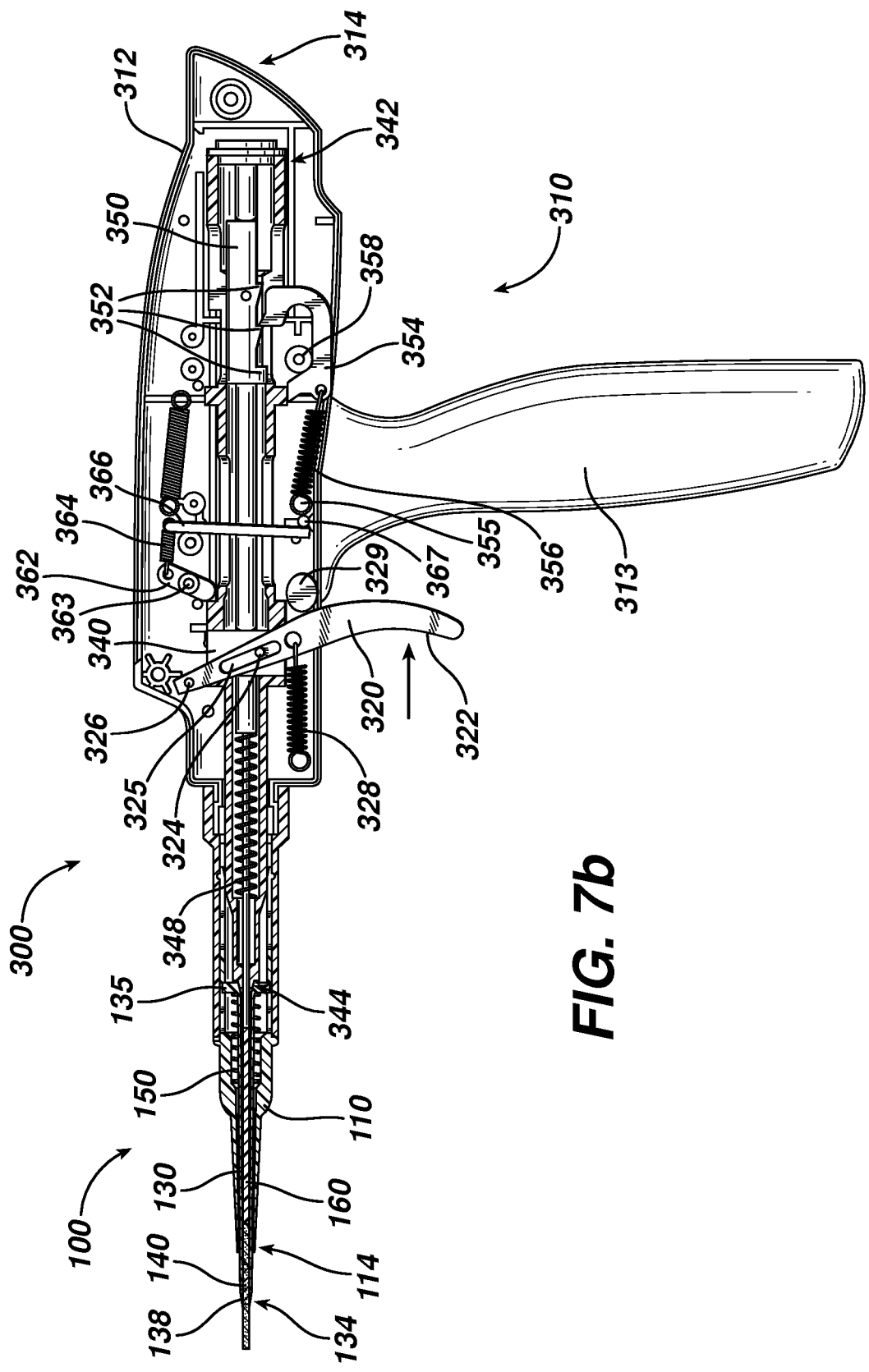
FIG. 7b is a cross-sectional side view of FIG. 7a after delivery of the first dose of medicament.

FIG. 7a shows medicament delivery device 300 according to the second embodiment of the present invention, prior to delivery of a first dose of the medicament. At this point, clutch 366 is in the immobilized condition, preventing the movement of ratchet 350. A dose of medicament 140 is delivered by pressing trigger 320 in the direction of the arrow in FIG. 7b. As trigger 320 is engaged with inner sleeve 340 via connection pin 324, the rotary movement of trigger 320 around pin 326 converts to a linear rearward (distal to proximal) motion of inner sleeve 340. As mentioned earlier, proximal end 132 of barrel 130 is aligned with inner sleeve shoulder 186 (see FIG. 5b). Cartridge spring 150 biases barrel 130 towards proximal end 132 to provide a distal to proximal (rearward) motion for barrel 130 when inner sleeve 340 moves towards proximal end 314 of handle case 312. At this point ratchet 350, which is engaged with the proximal end of SSM 160, is in the immobilized condition, so ratchet 350 and SSM 160 remain in a relative stationary position with respect to barrel 130 as barrel 130 moves towards proximal end 314 of handle case 312. The retracting motion of barrel 130 releases medicament 140 from distal opening 142 of barrel 130, delivering the medicament to the delivery site.

Upon rearward motion (distal to proximal) of the inner sleeve, ratchet pawl 354 is lifted by pawl pin 358 to release the pawl foot from first ratchet tooth 352, and move it to the second ratchet tooth 352. The axial movement of ratchet pawl 354 is then limited by pawl pin 358. Pawl spring 356 is now extended, and biases ratchet pawl 354 to remain engaged with second ratchet step 352. The motion of inner sleeve 340 also rotates clutch rotational lever 362, pulling clutch 366 to the proximal direction to release the immobilized condition. Inner sleeve spring 348 is compressed and trigger spring 328 is elongated. Rearward motion (distal to proximal) of trigger 320 is limited by trigger stop 329.

Figure 7C:
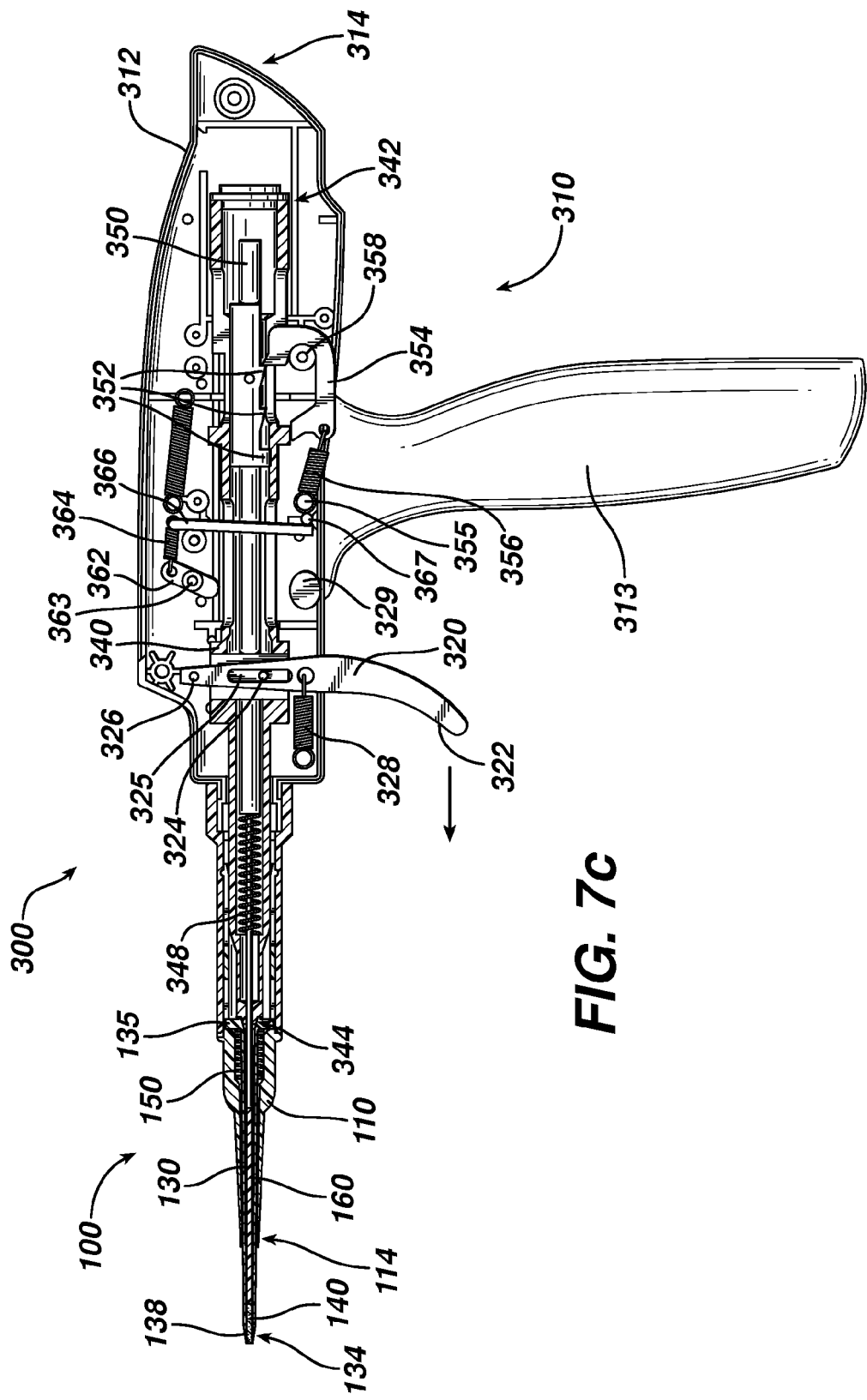
FIG. 7c is a cross-sectional side view of FIG. 7b when reset for delivery of a second dose of medicament.

Once medicament dose has been delivered, medicament delivery device 300 may be reset to prepare for next medicament delivery. Device 300 is reset by releasing trigger 320, which moves in the direction of the arrow in FIG. 7c. Inner sleeve 340 moves towards distal end 316 of handle case 312 due to the force exerted by the relaxation of trigger spring 328. Since ratchet 350, which is engaged with the proximal end of SSM 160, is no longer in the immobilized condition, ratchet 350 and SSM 160 move with inner sleeve 340 towards distal end 316 of handle case 312. As a result, distal end 134 of barrel 130 moves distally from distal end 114 of housing 110. Ratchet pawl 354 returns to its starting position, its axial movement limited by pawl pin 358. Pawl spring 356 also relaxes to its starting position. Device 300 is now reset for delivery of next dose of medicament.

Figure 8A:
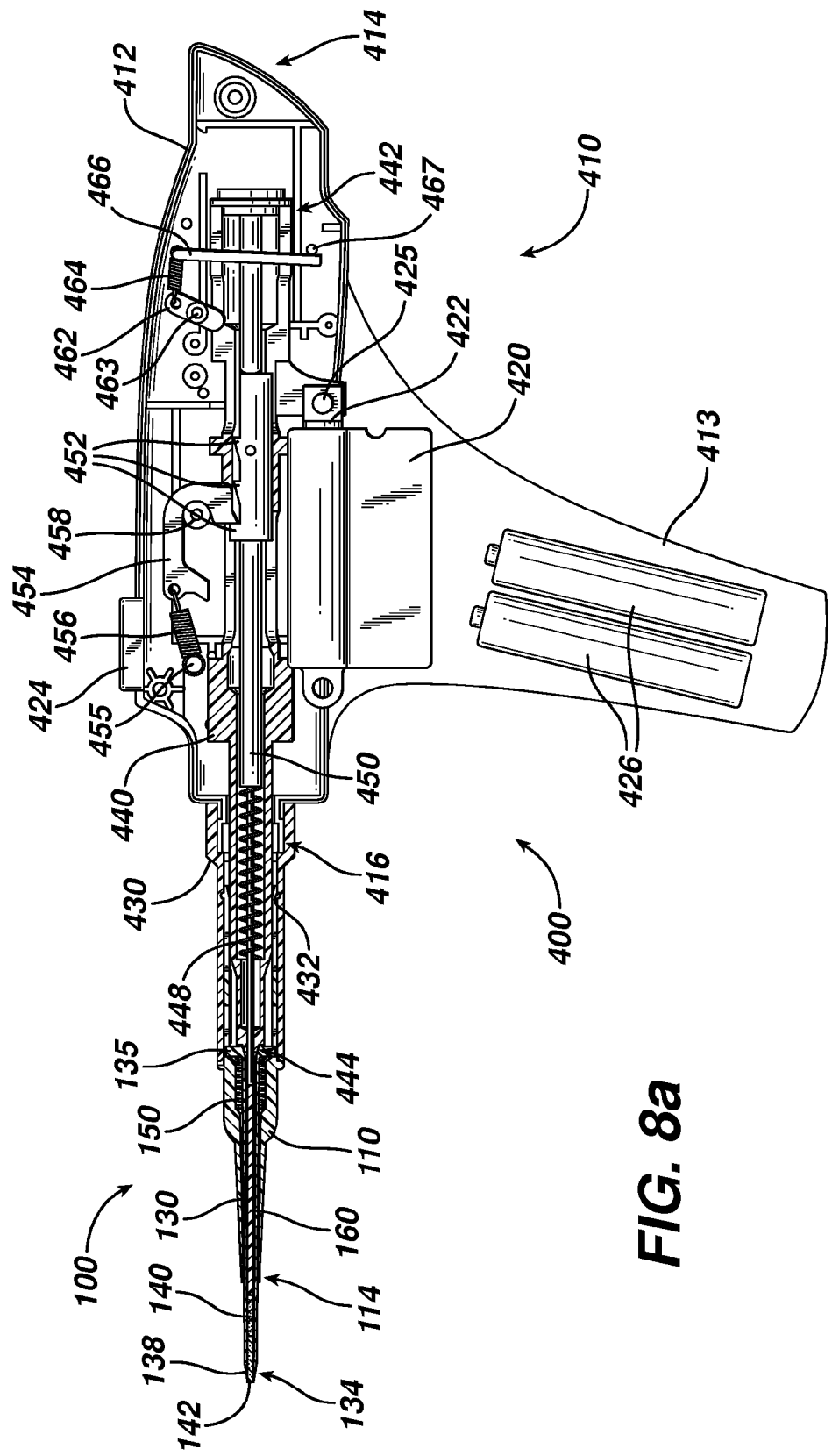
FIG. 8a is a partial cross-sectional side view of a third exemplary embodiment of the medicament delivery device according to the present invention, prior to delivery of a first dose of the medicament.

FIG. 8a is a partial cross-sectional side view of a third exemplary embodiment of the medicament delivery device according to the present invention. The figure shows device 400 comprised of cartridge 100 (as described in FIG. 4) and third embodiment actuator 410, which provides means for activating the means for retracting retractable barrel 130.

Actuator 410 is made with a handle case 412 and handle 413. All components of actuator 410 may be made from stainless steel, but could be made of any material that can be sterilized. Handle case and handle may be formed as two pieces that can be screwed together. Handle case 412 has a proximal portion 414 and a distal portion 416 having means for attaching cartridge 100. One suitable means for attaching the cartridge is a tube tip 430, which is positioned at the distal portion 416 of the actuator device and may be attached to the handle by threading it onto handle case 412. The tube tip may have an undercut 432 on its inner surface to retain cartridge 100.

In this third embodiment, actuator 410 converts a linear trigger motion to a proximal to distal linear motion. Actuator 410 has a linear displacement motor 420 located above handle 413. Motor 420 has a displacement rod 422, trigger 424, and power source 426. In this embodiment, power source 426 is a pair of batteries. It is to be understood that motor 420, trigger 424, and power source 426 are connected with wires (not shown), so that pressing trigger 424 actuates motor 420, allowing movement of displacement rod 422.

Also within handle case 412 is a cannulated inner sleeve 440 having a proximal portion 442, a tapered distal portion 444 for interfacing inner sleeve 440 with barrel extension 135 of barrel 130. Displacement rod 422 is engaged with inner sleeve 440 via connection pin 425.

Within the cannulation of inner sleeve 440 is inner sleeve spring 448, and inner ratchet 450 with at least one step 452 (three steps shown in FIG. 8a). The inner sleeve contains a recess for connecting a ratchet pawl 454 to the inner sleeve. The inner sleeve also contains a slot for maintaining the orientation between the pawl and the ratchet via a pin. A pawl spring 456 connects ratchet pawl 454 to a pin 455 in handle case 412. Pawl spring 456 biases ratchet pawl 454 to remain engaged with first ratchet step 452. The axial movement of ratchet pawl 454 is limited by pawl pin 458. The distal end of inner ratchet 450 is engaged with the proximal end of substantially stationary member (SSM) 160. Inner sleeve spring 448 is located within the cannulation of inner sleeve 440, surrounding distal portion of inner ratchet 450 and biasing the inner ratchet towards the proximal end 414 of handle case 412.

The proximal portion of the ratchet is placed in a clutch 466. The clutch 466 pivots about a pin 467 located on the handle case 412 to create an immobilized condition, which controls the motion of the ratchet only. A clutch rotational lever 462 rotates around a pin 463 mounted in handle case 412. The clutch rotational lever is connected to the clutch 466 via a spring 464, and controls the immobilized condition of clutch 466.

Figure 8B:
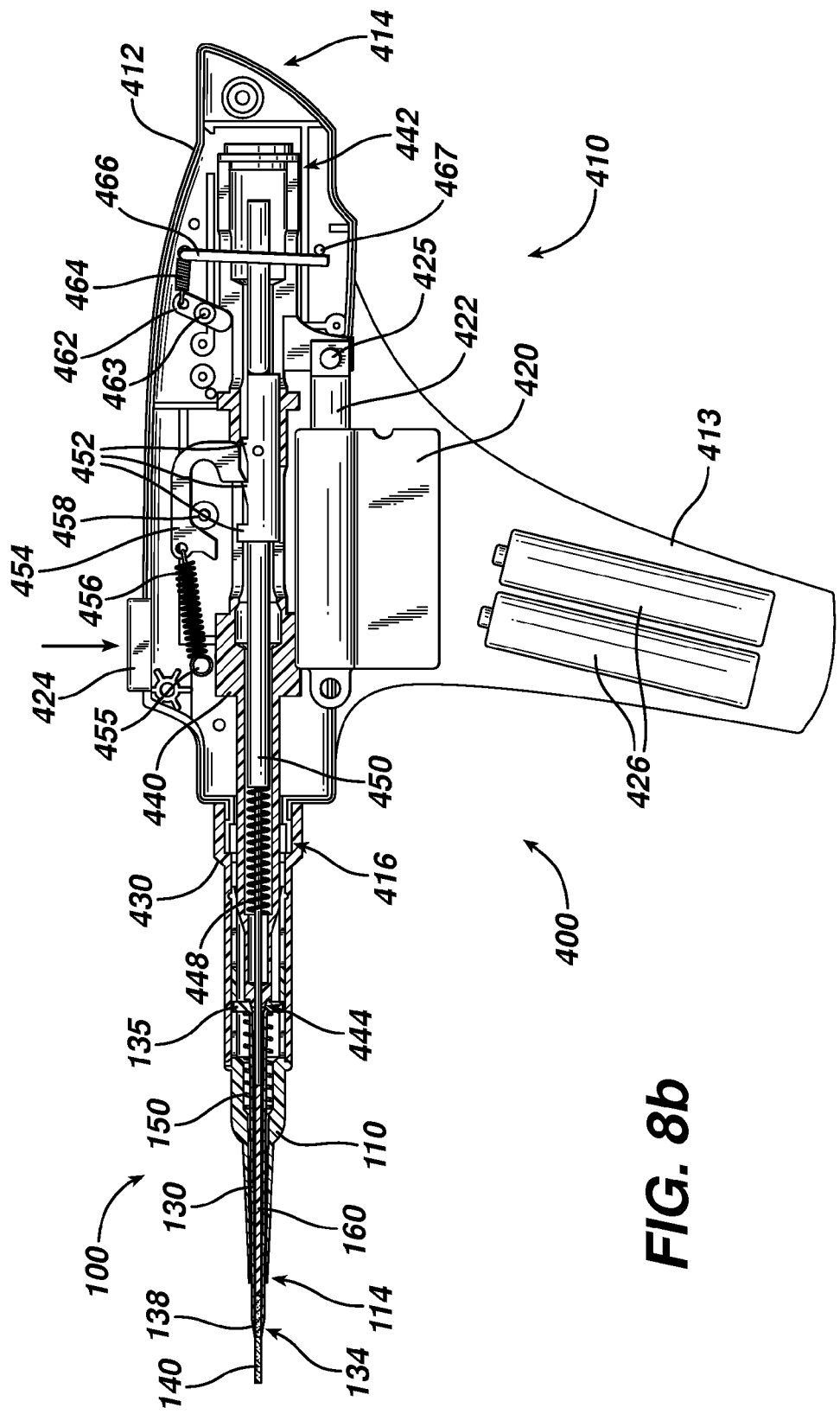
FIG. 8b is a cross-sectional side view of FIG. 8a after delivery of the first dose of medicament.

FIG. 8a shows medicament delivery device 400 according to the third embodiment of the present invention, prior to delivery of a first dose of the medicament. At this point, clutch 466 is in the immobilized condition, preventing the movement of ratchet 450. A dose of medicament 140 is delivered by pressing trigger 424 in the direction of the arrow in FIG. 8b. Pressing trigger 424 actuates motor 420, creating rearward (distal to proximal) movement of displacement rod 422.

As displacement rod 422 is engaged with inner sleeve 440 via connection pin 425 rearward (distal to proximal) motion of displacement rod 422 is results in rearward motion of inner sleeve 440. As mentioned earlier, proximal end 132 of barrel 130 is aligned with inner sleeve shoulder 186 (see FIG. 5b). Cartridge spring 150 biases barrel 130 towards proximal end 132 to provide a distal to proximal motion for barrel 130 when inner sleeve 440 moves towards proximal end 414 of handle case 412. At this point ratchet 450, which is engaged with the proximal end of SSM 160, is in the immobilized condition, so ratchet 450 and SSM 160 remain in a relative stationary position with respect to barrel 130 as barrel 130 moves towards proximal end 414 of handle case 412. The retracting motion of barrel 130 releases medicament 140 from distal opening 142 of barrel 130, delivering the medicament to the delivery site.

Upon rearward motion (distal to proximal) of the inner sleeve, ratchet pawl 454 is lifted by pawl pin 458 to release the pawl foot from first ratchet tooth 452, and move it to the second ratchet tooth. The axial movement of ratchet pawl 454 is then limited by pawl pin 458. Pawl spring 456 is now extended, and biases ratchet pawl 454 to remain engaged with second ratchet step 452. The motion of inner sleeve 440 also rotates clutch rotational lever 462, pulling clutch 466 to the proximal direction to release the immobilized condition. At this point, inner sleeve spring 448 is compressed.

Once medicament dose has been delivered, medicament delivery device 400 may be reset to prepare for next medicament delivery. Though not shown, device 400 is reset by reversing movement of displacement rod 422. Inner sleeve 440 moves towards distal end 416 of handle case 412. Since ratchet 450, which is engaged with the proximal end of SSM 160, is no longer in the immobilized condition, ratchet 450 and SSM 160 move with inner sleeve 440 towards distal end 416 of handle case 412. As a result, distal end 134 of barrel 130 moves distally from distal end 114 of housing 110. Ratchet pawl 454 returns to its starting position, its axial movement limited by pawl pin 458. Pawl spring 456 also relaxes to its starting position. Device 400 is now reset for delivery of next dose of medicament.

Also included in this disclosure is a fourth embodiment of actuator for medicament delivery according to the present invention. This embodiment is shown in FIGS. 9a and 9b. In this embodiment, actuator 510, which provides means for activating the means for retracting retractable barrel 130 of cartridge 100 (as described in FIG. 4), converts a linear trigger motion to a proximal to distal linear motion. Actuator 510 is made with a handle case 512 and trigger 520. Handle case 512 has a proximal portion 514 and a distal portion 516. Trigger 520 has ring components 521 and 522, trigger block 524, spring plate 526, and spring 528. Ring components 521 and 522 are affixed to trigger block 524, while spring 528 is fixed between spring plate 526 and distal end of handle case 512.

Also within handle case 512 is a cannulated inner sleeve 540 having a proximal portion 542, a tapered distal portion 544 for interfacing inner sleeve 540 with retractable chamber of cartridge (not shown). Within the cannulation of inner sleeve 540 is inner ratchet 550 with at least one step 552 (three steps shown in FIG. 9b). The inner sleeve contains a recess for connecting a ratchet pawl 554 to the inner sleeve. The inner sleeve also contains a slot for maintaining the orientation between the pawl and the ratchet. A pawl pin 556 to handle case 512. Pawl pin 556 biases ratchet pawl 554 to remain engaged with first ratchet step 552. The distal end of inner ratchet 550 is engaged with the proximal end of substantially stationary member SSM 160 of cartridge 100 (not shown).

First pulley 562 and second pulley 564 are mounted on inner sleeve 540 and trigger block 524, respectively. Belt 566 is attached to spring plate 526 and ring component 522, and overlaps pulleys 562 and 564. The proximal portion of inner ratchet 550 is placed in a clutch 576. The clutch 576 creates an immobilized condition, which controlled the motion of the ratchet only.

Prior to delivery of a first dose of the medicament, clutch 576 is in the immobilized condition, preventing the movement of ratchet 550. A dose of medicament is delivered by pressing trigger 520 from the proximal portion 514 towards the distal portion 516 of handle case 512. This proximal to distal motion of trigger 520 is converted to a distal to proximal (rearward) motion of inner sleeve 540 by the actions of pulleys 562 and 564. As in all other embodiments, the rearward motion of inner sleeve 540 results in a rearward motion of the barrel of the medicament cartridge. Since ratchet 550, which is engaged with the proximal end of SSM 160, is in the immobilized condition, ratchet 550 and SSM 160 remain in a relative stationary position with respect to the barrel. The retracting motion of the barrel releases the medicament from the distal opening of the barrel, delivering the medicament to the delivery site.

Also included in this disclosure is a fifth embodiment of actuator for medicament delivery according to the present invention. This embodiment is shown in FIGS. 10a and 10b. The figures show device 600 comprised of cartridge 100 (as described in FIG. 4) and fifth embodiment actuator 610, which provides means for activating the means for retracting retractable barrel 130.

Actuator 610 is made with a handle case 612. The handle case, as well as all other components of actuator 610, may be made from stainless steel, but could be made of any material that can be sterilized. Handle case 612 may be formed as 2 pieces that can be screwed together, and is designed to provide means for gripping the actuator. Handle case 612 has a proximal end 614 and a distal end 616. Distal end 616 has means for attaching cartridge 100. One suitable means for attaching the cartridge is a tube tip 630 that is positioned at the distal end 616 of the actuator device and may be attached to the handle by threading it onto handle case 612. The tube tip may have an undercut 632 on its inner surface to retain cartridge 100.

In this embodiment, actuator 610 converts a linear trigger motion to a proximal to distal linear motion. Actuator 610 has trigger button 620 located on the upper surface at distal end 616 of handle case 612. Trigger button 620 has a catch 622, a flexure spring 624, and a catch spring 626. Within handle case 612 is a cannulated inner sleeve 640 having a proximal portion 642, a tapered distal portion 644 for interfacing inner sleeve 640 with barrel extension 135 of barrel 130, and a recess for engaging catch 622 of trigger button 620.

Within the cannulation of inner sleeve 640 is inner ratchet 650 with at least one step 652 (three steps shown in FIG. 10b). Catch spring 626 biases catch 622 to remain engaged with first ratchet step 652. The distal end of inner ratchet 650 is engaged with the proximal end of stationary substantially stationary member (SSM) 160.

Inner ratchet 650 is placed in a clutch 664. Clutch springs 666 create an immobilized condition for clutch 664, which controls the motion of the ratchet only. The proximal end of inner ratchet 650 has a radial spring 658 engaging inner ratchet with thumb button 660. Thumb button 660 is cannulated, and inner ratchet return spring 672 is located in the cannulation of thumb button 660. Inner ratchet return spring 672 biases inner ratchet 650 towards distal end 616 of handle case 612.

FIG. 10b shows medicament delivery device 600 according to the present invention, prior to delivery of a first dose of the medicament. At this point, clutch 664 is not in the immobilized condition, allowing the movement of inner ratchet 650. Radial spring 658 engages inner ratchet 650 with thumb button 660, so moving thumb button 660 will move inner ratchet 650. Catch 622 is engaged with first ratchet step 652 and inner sleeve 640, held in that position by catch spring 626. Catch spring 626 also biases trigger button 620 radially outward from handle case 612.

A dose of medicament is delivered in two steps. In the first step, thumb button 660 is pressed towards the distal end 616 of handle case 612. Since inner ratchet 650 is engaged with thumb button 660, inner ratchet moves towards the distal end 616 of handle case 612. Likewise, inner sleeve 640, which is engaged with inner ratchet 650, moves towards the distal end 616 of handle case 612. Also, barrel 130, which is engaged with inner sleeve 640, moves towards the distal end 114 of housing 110. Cartridge spring 150 is compressed, creating a bias for moving barrel 130 and inner sleeve 640 towards the proximal end 614 of handle case 612. Clutch springs 666 are elongated, creating an immobilized condition for clutch 664.

In the second step, trigger button 620 is depressed into handle case 612. Catch spring 626 is compressed, disengaging catch 622 from first ratchet step 652. Catch 622 passes form first to second ratchet step 652. Cartridge spring 150 now elongates, moving barrel 130 and inner sleeve 640 towards the proximal end 614 of handle case 612. Since clutch 664 is in the immobilized condition, inner ratchet 650 and SSM 160 remain in a relative stationary position with respect to barrel 130 as barrel 130 moves towards proximal end 614 of handle case 612. The retracting motion of barrel 130 releases medicament from distal opening 142 of barrel 130, delivering the medicament to the delivery site.

Figure 11C:
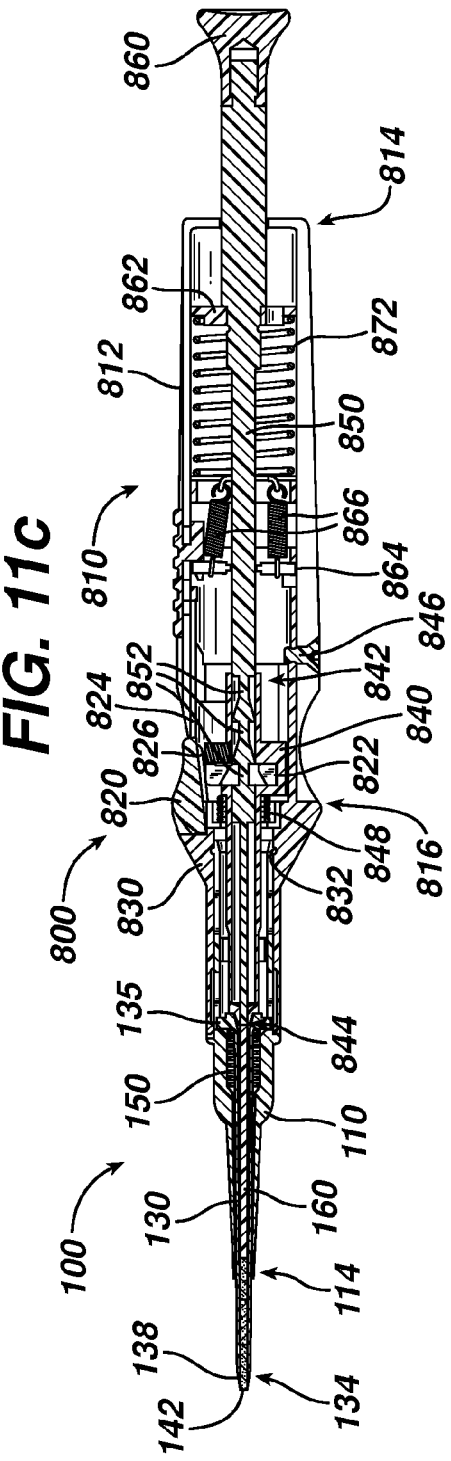
FIG. 11c is a cross-sectional side view of FIG. 11b as delivery of the first dose of medicament is performed.

Also included in this disclosure is a sixth embodiment of actuator for medicament delivery according to the present invention. This embodiment is shown in FIGS. 11a through 11j. The figures show device 800 comprised of cartridge 100 (as described in FIG. 4) and sixth embodiment actuator 810, which provides means for activating the means for retracting retractable barrel 130. FIG. 11a shows optional retaining cap 170 disposed on distal tip 138 to protect the medicament from contamination.

Actuator 810 is made with an outer handle case 812. The handle case, as well as all other components of actuator 810, may be made from stainless steel, but could be made of any material that can be sterilized. Handle case 812 may be formed as two pieces that can be screwed together, and is designed to provide means for gripping the actuator. Handle case 812 has a proximal end 814 and a distal end 816. Distal end 816 has means for attaching cartridge 100. One suitable means for attaching the cartridge is a tube tip 830 that is positioned at the distal end 816 of the actuator device and may be attached to the handle by threading it onto handle case 812. The tube tip may have an undercut 832 on its inner surface to retain cartridge 100.

In this embodiment, actuator 810 converts a linear trigger motion to a proximal to distal linear motion. Actuator 810 has trigger button 820 located on the upper surface at distal end 816 of handle case 812. Trigger button 820 has a flexure spring 824 for biasing trigger button 820 towards the upper surface of handle case 812. Within handle case 812 is a catch 822 and a catch spring 826, as well as a cannulated inner sleeve 840 having a proximal portion 842, a tapered distal portion 844 for interfacing inner sleeve 840 with barrel extension 135 of barrel 130, and a recess for engaging catch 822.

Within the cannulation of inner sleeve 840 is inner sleeve spring 848, and inner ratchet 850 with at least one step 852 (three steps shown in FIGS. 11a through 11j). Catch spring 826 biases catch 822 to remain engaged with first ratchet step 852. Distal end of inner ratchet 850 is engaged with the proximal end of substantially stationary member (SSM) 160 when device 800 is operational.

Inner sleeve spring 848 is located within the cannulation of inner sleeve 840, surrounding the distal portion of inner ratchet 850, and biasing inner ratchet 850 towards the proximal end 814 of handle case 812. Inner sleeve stop 846 prevents inner sleeve 840 from progressing towards the proximal end 814 of handle case 812.

Inner ratchet 850 is placed in a clutch 864. Clutch springs 866 create an immobilized condition for clutch 864, which controls the motion of the ratchet only. Inner ratchet catch 862 is attached to inner ratchet 850 and is sized to prevent inner ratchet 850 from being removed from handle case 812. Inner ratchet return spring 872 is located in handle case 812. Inner ratchet return spring 872 is engaged with inner ratchet catch 862, and biases inner ratchet 850 towards distal end 816 of handle case 812. Inner ratchet cap 860 may be disposed on proximal end of inner ratchet 850 to provide comfort for the user of device 800.

FIG. 11a shows the sixth exemplary embodiment of the medicament delivery device prior to connection between cartridge 100 and actuator 810. As shown in FIG. 11a, barrel 130 and SSM 160 are aligned with inner ratchet 850 prior to connection between cartridge 100 and actuator 810.

To complete the connection of actuator 810 to cartridge 100, inner ratchet 850 is moved distally (in the direction of SSM 160). This may be achieved by the user by holding handle case 812 stationary in the palm of the hand and pressing on inner ratchet cap 860 with the user's thumb. Since inner ratchet 850 is engaged with thumb button 860, inner ratchet moves towards the distal end 816 of handle case 812. Likewise, inner sleeve 840, which is engaged with inner ratchet 850, moves towards the distal end 816 of handle case 812. Also, barrel 130, which is engaged with inner sleeve 840, moves towards the distal end 114 of housing 110. Cartridge spring 150 and inner sleeve spring 848 are compressed, creating a bias for moving barrel 130 and inner sleeve 840 towards the proximal end 814 of handle case 812. Clutch springs 866 remain elongated, creating an immobilized condition for clutch 864.

FIG. 11b shows the sixth exemplary embodiment of the medicament delivery device after connection between cartridge 100 and actuator 810. As shown in FIG. 11b, cartridge spring 150 and inner sleeve spring 848 are in a compressed state, distal portion of inner ratchet 850 is engaged with the proximal end of SSM 160, trigger button 820 is aligned with catch 822 and catch spring 826, and inner ratchet return spring 872 is partially compressed. Catch 822 is engaged with first ratchet step 852 and inner sleeve 840, held in that position by catch spring 826. Catch spring 826 and flexural spring 824 also bias trigger button 820 radially outward from handle case 812.

Figure 11D:
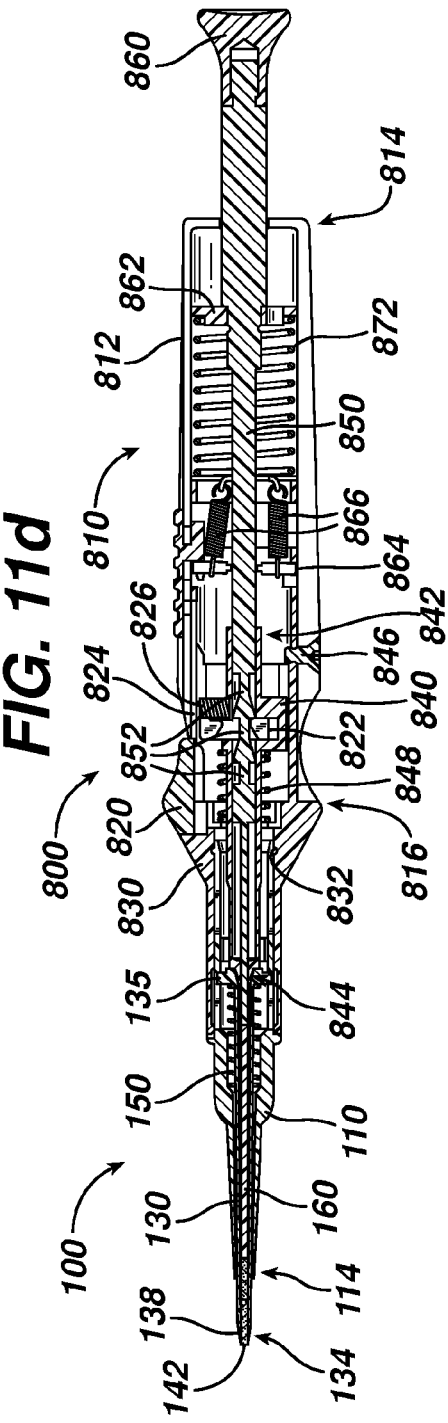
FIG. 11d is a cross-sectional side view of FIG. 11c after delivery of the first dose of medicament.

To deliver a first dose of medicament, trigger button 820 is depressed into handle case 812. As shown in FIG. 11c, catch spring 826 is compressed, disengaging catch 822 from first ratchet step 852. Catch 822 passes from first to second ratchet step 852. As shown in FIG. 11d, cartridge spring 150 and inner sleeve spring 848 now elongate, moving barrel 130, inner sleeve 840, catch 822 and catch spring 826 towards the proximal end 814 of handle case 812. Since clutch 864 is in the immobilized condition, inner ratchet 850 and SSM 160 remain in a relative stationary position with respect to barrel 130 as barrel 130 moves towards proximal end 814 of handle case 812. The retracting motion of barrel 130 releases medicament from distal opening 142 of barrel 130, delivering the first dose of medicament to the delivery site.

To reset device 800 for delivery of a second dose of medicament, user holds handle case 812 stationary in the palm of the hand and presses on inner ratchet cap 860 with the user's thumb. Inner ratchet 850, engaged with thumb button 860, moves towards the distal end 816 of handle case 812. Likewise, inner sleeve 840, engaged with inner ratchet 850, moves towards the distal end 816 of handle case 812. Finally, barrel 130, engaged with inner sleeve 840, moves towards the distal end 114 of housing 110. Cartridge spring 150 and inner sleeve spring 848 are compressed, creating a bias for moving barrel 130 and inner sleeve 840 towards the proximal end 814 of handle case 812. Clutch springs 866 are elongated, creating an immobilized condition for clutch 864.

FIG. 11e shows the sixth exemplary embodiment of the medicament delivery device reset for delivery of second medicament dose. As shown in FIG. 11e, cartridge spring 150 and inner sleeve spring 848 are in a compressed state, trigger button 820 is aligned with catch 822 and catch spring 826, and inner ratchet return spring 872 is more compressed than prior to first dose. Catch 822 is engaged with second ratchet step 852 and inner sleeve 840, held in that position by catch spring 826. Catch spring 826 and flexural spring 824 also bias trigger button 820 radially outward from handle case 812.

To deliver a second dose of medicament, trigger button 820 is depressed into handle case 812. As shown in FIG. 11f, catch spring 826 is compressed, disengaging catch 822 from second ratchet step 852. Catch 822 passes from second to third ratchet step 852. As shown in FIG. 11g, cartridge spring 150 and inner sleeve spring 848 now elongate, moving barrel 130, inner sleeve 840, catch 822 and catch spring 826 towards the proximal end 814 of handle case 812. Since clutch 864 is in the immobilized condition, inner ratchet 850 and SSM 160 remain in a relative stationary position with respect to barrel 130 as barrel 130 moves towards proximal end 814 of handle case 812. The retracting motion of barrel 130 releases medicament from distal opening 142 of barrel 130, delivering the second dose of medicament to the delivery site.

To reset device 800 for delivery of a third dose of medicament, user holds handle case 812 stationary in the palm of the hand and presses on inner ratchet cap 860 with the user's thumb. Inner ratchet 850, engaged with thumb button 860, moves towards the distal end 816 of handle case 812. Likewise, inner sleeve 840, engaged with inner ratchet 850, moves towards the distal end 816 of handle case 812. Finally, barrel 130, engaged with inner sleeve 840, moves towards the distal end 114 of housing 110. Cartridge spring 150 and inner sleeve spring 848 are compressed, creating a bias for moving barrel 130 and inner sleeve 840 towards the proximal end 814 of handle case 812. Clutch springs 866 remain elongated, creating an immobilized condition for clutch 864.

FIG. 11h shows the sixth exemplary embodiment of the medicament delivery device reset for delivery of a third medicament dose. As shown in FIG. 11h, cartridge spring 150 is in a compressed state, trigger button 820 is aligned with catch 822 and catch spring 826, and inner ratchet return spring 872 is more compressed than prior to first dose. Catch 822 is engaged with third ratchet step 852 and inner sleeve 840, held in that position by catch spring 826. Catch spring 826 and flexural spring 824 also biases trigger button 820 radially outward from handle case 812.

To deliver a third dose of medicament, trigger button 820 is depressed into handle case 812. As shown in FIG. 11i, catch spring 826 is compressed, disengaging catch 822 from third ratchet step 852. As shown in FIG. 11j, cartridge spring 150 and inner sleeve spring 848 now elongate, moving barrel 130, inner sleeve 840, catch 822 and catch spring 826 towards the proximal end 814 of handle case 812. Since clutch 864 is in the immobilized condition, inner ratchet 850 and SSM 160 remain in a relative stationary position with respect to barrel 130 as barrel 130 moves towards proximal end 814 of handle case 812. The retracting motion of barrel 130 releases medicament from distal opening 142 of barrel 130, delivering the third dose of medicament to the delivery site.

Figure 12C:
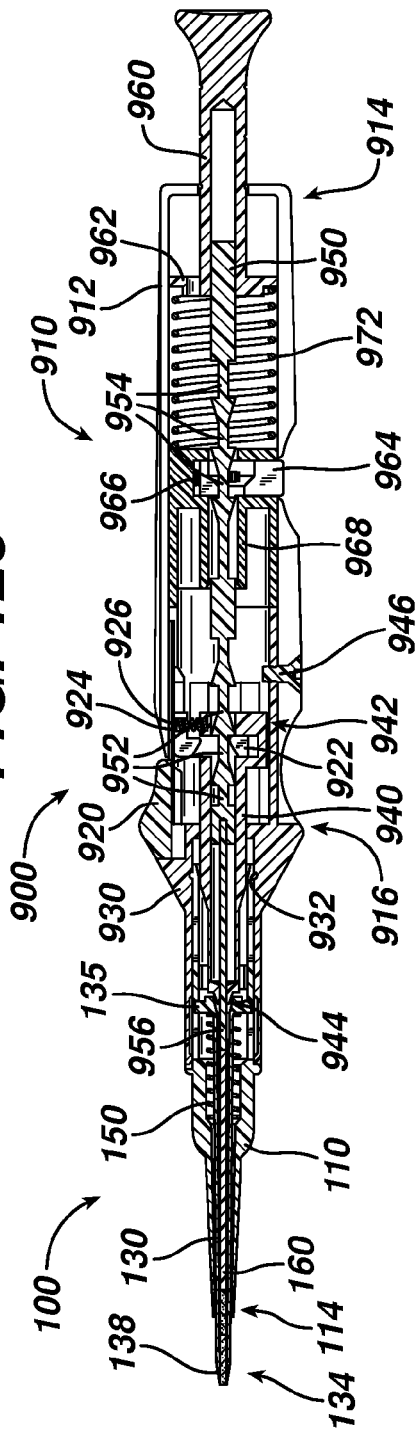
FIG. 12c is a cross-sectional side view of FIG. 12b after delivery of the first dose of medicament.

Also included in this disclosure is a seventh embodiment of actuator for medicament delivery according to the present invention. This embodiment is shown in FIGS. 12a through 12e. The figures show device 900 comprised of cartridge 100 (as described in FIG. 4) and seventh embodiment actuator 910, which provides means for activating the means for retracting retractable barrel 130. FIG. 12a shows optional retaining cap 170 disposed on distal tip 138 to protect the medicament from contamination.

Actuator 910 is made with an outer handle case 912. The handle case, as well as all other components of actuator 910, may be made from stainless steel, but could be made of any material that can be sterilized. Handle case 912 may be formed as two pieces that can be screwed together, and is designed to provide means for gripping the actuator. Handle case 912 has a proximal end 914 and a distal end 916. Distal end 916 has means for attaching cartridge 100. One suitable means for attaching the cartridge is a tube tip 930 that is positioned at the distal end 916 of the actuator device and may be attached to the handle by threading it onto handle case 912. The tube tip may have an undercut 932 on its inner surface to retain cartridge 100.

In this embodiment, actuator 910 converts a linear trigger motion to a proximal to distal linear motion. Actuator 910 has trigger button 920 located on the upper surface at distal end 916 of handle case 912. Trigger button 920 has a flexure spring 924 for biasing trigger button 920 towards the upper surface of handle case 912. Within handle case 912 is a catch 922 and a catch spring 926, as well as a cannulated inner sleeve 940 having a proximal portion 942, a tapered distal portion 944 for interfacing inner sleeve 940 with barrel extension 135 of barrel 130, and a recess for engaging catch 922.

Within the cannulation of inner sleeve 940 is inner ratchet 950 with at least one catch step 952 (three steps shown in FIGS. 12a through 12e). Catch spring 926 biases catch 922 to remain engaged with first catch step 952. Distal end of inner ratchet 950 is engaged with the proximal end of rod 956, which, in turn is engaged with substantially stationary member (SSM) 160 when device 900 is operational.

Spring 150 is engaged with the tapered distal portion 944 of inner sleeve 940, and biases inner sleeve 940 towards the proximal end 914 of handle case 912. Inner sleeve stop 946 prevents inner sleeve 940 from progressing towards the proximal end 914 of handle case 912.

Inner ratchet 950 is disposed in a ratchet guide 968 and a gate 964. Gate spring 966 biases gate 964 to remain engaged with inner ratchet 950 distal to first gate step 954, preventing distal to proximal movement of inner ratchet 950. Inner ratchet 950 is disposed in cannulation of plunger 960. Plunger catch 962 is attached to plunger 960 and is sized to prevent inner ratchet 950 from being removed from handle case 912. Inner ratchet return spring 972 is located in handle case 912. Inner ratchet return spring 972 is engaged with plunger catch 962, and biases inner ratchet 950 towards distal end 916 of handle case 912.

FIG. 12a shows the seventh exemplary embodiment of the medicament delivery device prior to connection between cartridge 100 and actuator 910. Barrel 130 and SSM 160 are aligned with inner ratchet 950 prior to connection between cartridge 100 and actuator 910.

To complete the connection of actuator 910 to cartridge 100, inner ratchet 950 is moved distally. This may be achieved by the user by holding handle case 912 stationary in the palm of the hand and pressing on plunger 960 with the user's thumb. Since inner ratchet 950 is engaged with plunger 960, inner ratchet moves towards the distal end 916 of handle case 912. Likewise, inner sleeve 940, which is engaged with inner ratchet 950, moves towards the distal end 916 of handle case 912. Also, barrel 130, which is engaged with inner sleeve 940, moves towards the distal end 114 of housing 110. Cartridge spring 150 is compressed, creating a bias for moving barrel 130 and inner sleeve 940 towards the proximal end 914 of handle case 912. As inner ratchet 950 moves towards the distal end 916 of handle case 912, gate 964 passes to first gate step 954. Gate spring 966 remains elongated, biasing gate 964 to remain engaged with first gate step 954, preventing distal to proximal movement of inner ratchet 950.

FIG. 12b shows the seventh exemplary embodiment of the medicament delivery device after connection between cartridge 100 and actuator 910. As shown in the figure, cartridge spring 150 is in a compressed state, distal portion of inner ratchet 950 is engaged with the proximal end of rod 956, which, in turn is engaged with SSM 160, trigger button 920 is aligned with catch 922 and catch spring 926, and inner ratchet return spring 972 is partially compressed. Catch 922 is engaged with first ratchet step 952 and inner sleeve 940, is held in that position by catch spring 926. Catch spring 926 and flexural spring 924 also bias trigger button 920 radially outward from handle case 912. Gate spring 966 remains elongated, gate 964 remains engaged with first gate step 954, preventing distal to proximal movement of inner ratchet 950.

To deliver a first dose of medicament, trigger button 920 is depressed into handle case 912. Catch spring 926 is compressed, disengaging catch 922 from first ratchet step 952. Catch 922 passes from first to second ratchet step 952. Cartridge spring 150 elongates, moving barrel 130, inner sleeve 940, catch 922 and catch spring 926 towards the proximal end 914 of handle case 912. Since inner ratchet 950 is not able to move in a distal to proximal direction, inner ratchet 950 and SSM 160 remain in a relative stationary position with respect to barrel 130 as barrel 130 moves proximal end 914 of handle case 912. The retracting motion of barrel 130 releases medicament from distal opening 142 of barrel 130, delivering the first dose of medicament to the delivery site.

As shown in FIG. 12c, cartridge spring 150 is in an elongated state, distal portion of inner ratchet 950 is engaged with the proximal end of rod 956, which, in turn is engaged with SSM 160. Trigger button 920 is no longer aligned with catch 922 and catch spring 926, and inner ratchet return spring 972 is partially compressed. Catch 922 is engaged with second ratchet step 952 and inner sleeve 940, and is held in that position by catch spring 926. Catch spring 926 and flexural spring 924 also bias trigger button 920 radially outward from handle case 912. Gate spring 966 remains elongated, gate 964 remains engaged with first gate step 954, and inner ratchet 950 is not able to move in a distal to proximal direction.

To reset device 900 for delivery of a second dose of medicament, user holds handle case 912 stationary in the palm of the hand and presses on plunger 960 with the user's thumb. Inner ratchet 950, engaged with plunger 960, moves towards the distal end 916 of handle case 912. Likewise, inner sleeve 940, engaged with inner ratchet 950, moves towards the distal end 916 of handle case 912. Finally, barrel 130, engaged with inner sleeve 940, moves towards the distal end 114 of housing 110. Cartridge spring 150 is compressed, creating a bias for moving barrel 130 and inner sleeve 940 towards the proximal end 914 of handle case 912. As inner ratchet 950 moves towards the distal end 916 of handle case 912, gate 964 passes from first to second gate step 954. Gate spring 966 remains elongated, biasing gate 964 to remain engaged with second gate step 954, preventing distal to proximal movement of inner ratchet 950.

Figure 12D:
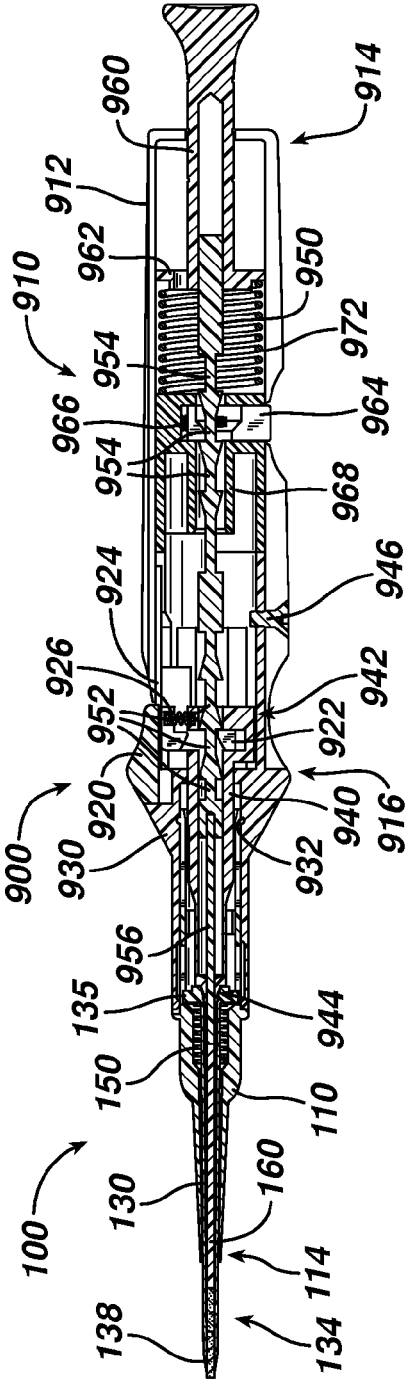
FIG. 12d is a cross-sectional side view of FIG. 12c when reset for delivery of a second dose of medicament.

FIG. 12d shows the seventh exemplary embodiment of the medicament delivery device reset for delivery of second medicament dose. As shown in the figure, cartridge spring 150 is in a compressed state, trigger button 920 is aligned with catch 922 and catch spring 926, and inner ratchet return spring 972 is more compressed than prior to first dose. Catch 922 is engaged with second ratchet step 952 and inner sleeve 940, and held in that position by catch spring 926. Catch spring 926 and flexural spring 924 also biases trigger button 920 radially outward from handle case 912.

To deliver a second dose of medicament, trigger button 920 is depressed into handle case 912. Catch spring 926 is compressed, disengaging catch 922 from second ratchet step 952. Catch 922 passes from second to third catch step 952. Cartridge spring 150 elongates, moving barrel 130, inner sleeve 940, catch 922 and catch spring 926 towards the proximal end 914 of handle case 912. Since inner ratchet 950 is not able to move in a distal to proximal direction, inner ratchet 950 and SSM 160 remain in a relative stationary position with respect to barrel 130 as barrel 130 moves towards proximal end 914 of handle case 912. The retracting motion of barrel 130 releases medicament from distal opening 142 of barrel 130, delivering the second dose of medicament to the delivery site.

Figure 12E:
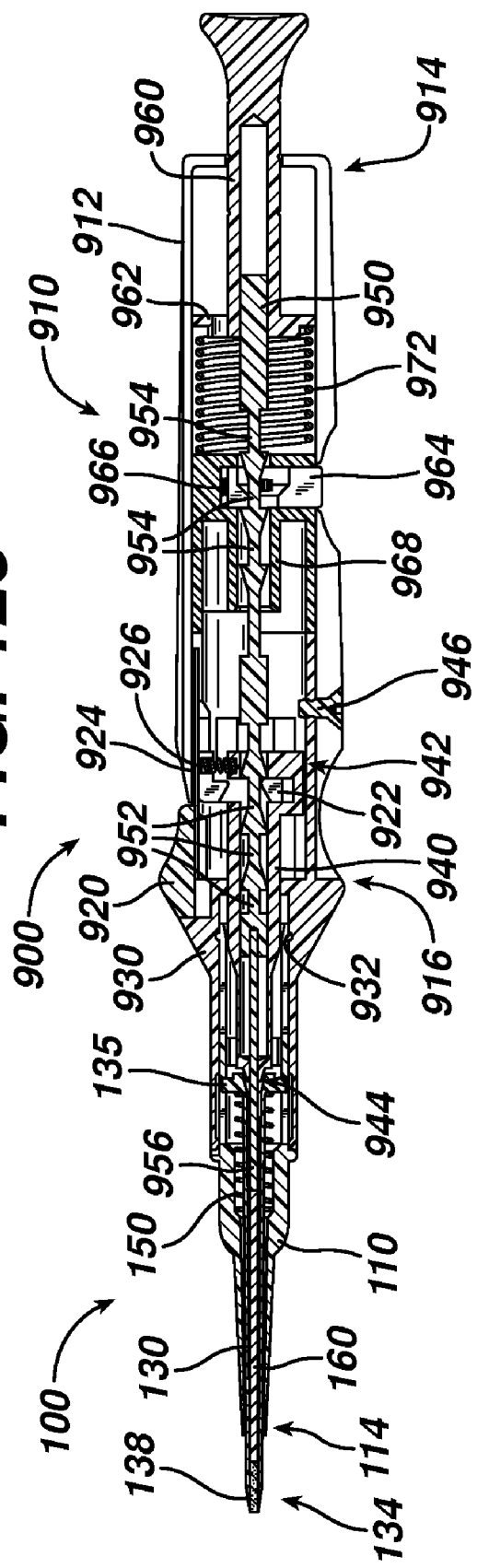
FIG. 12e is a cross-sectional side view of FIG. 12d after delivery of the second dose of medicament.

As shown in FIG. 12e, cartridge spring 150 is in an elongated state, distal portion of inner ratchet 950 is engaged with the proximal end of rod 956, which, in turn is engaged with SSM 160. Trigger button 920 is no longer aligned with catch 922 and catch spring 926, and inner ratchet return spring 972 is more compressed than after delivery of first dose. Catch 922 is engaged with third ratchet step 952 and inner sleeve 940, and is held in that position by catch spring 926. Catch spring 926 and flexural spring 924 also bias trigger button 920 radially outward from handle case 912. Gate spring 966 remains elongated, gate 964 remains engaged with second gate step 954, and inner ratchet 950 is not able to move in a distal to proximal direction.

We claim:

1. A device for inserting a medicament within a body cavity of a mammal, said device comprising:
    a cartridge for containing said medicament therein, said cartridge comprising,
        a housing comprising a proximal portion and a distal portion,
        a retractable chamber disposed within said housing, said retractable chamber comprising an internal surface, an external surface and a lumen defined by said internal surface,
        a substantially stationary member disposed within said lumen of said retractable chamber, said substantially stationary member having a uniform cross-section sized to provide a sliding fit within said lumen to provide for retraction of said retractable chamber about said substantially stationary member upon actuation of said device; and
        means for retracting said retractable chamber about said substantially stationary member while maintaining said substantially stationary member in a substantially stationary position upon actuation of said device; and
    an actuator for placing said device in operation, said actuator comprising,
        means for activating said means for retracting said retractable chamber; and
    a handle case comprising a distal portion comprising means for attaching said actuator to said cartridge,
    wherein said proximal portion of said housing comprises means for connecting said cartridge to said actuator, and wherein said proximal portion of said housing is connected to said distal portion of said handle case, whereby said cartridge and said actuator are connected in operational engagement.

2. The device of claim 1 wherein a distal tip of said retractable chamber has a uniform external cross-section sized to fit within said body cavity.

3. The device of claim 1 wherein said means for retracting said retractable chamber comprises a spring disposed about said retractable chamber for retracting said retractable chamber about said substantially stationary member.

4. The device of claim 1 further comprising said medicament disposed within said chamber.

5. The device of claim 4 comprising multiple doses of said medicament.

6. The device of claim 4 wherein said medicament comprises a dry microparticle composition.

7. The device of claim 4 wherein said medicament is selected from the group consisting of antibacterials, antibiotics, antifungal agents, anti-inflammatory agents, immunosuppressive agents, immunostimulatory agents, dentinal desensitizers, odor masking agents, immune reagents, anesthetics, antiseptics, nutritional agents, antioxidants, lipopolysaccharide complexing agents, peroxides and growth factors.

8. The device of claim 4 wherein said medicament is selected from the group consisting of doxycycline, a pharmaceutically acceptable salt of doxycycline, hydrates of doxycycline, hydrates of a pharmaceutically acceptable salt of doxycycline, minocycline, a pharmaceutically acceptable salt of minocycline, hydrates of minocycline and hydrates of a pharmaceutically acceptable salt of minocycline.

9. The device of claim 1 wherein said cavity is a periodontal pocket of said mammal.

10. The device of claim 8 wherein said cavity is a periodontal pocket of said mammal.

11. The device of claim 1 comprising means for creating a linear motion effective to provide for retraction of said retractable chamber about said substantially stationary member upon activation of said device.

12. The device of claim 11 wherein said linear motion is in a distal to proximal direction with respect to said device.

13. The device of claim 1 wherein said means for attaching said actuator to said cartridge located at said distal portion of said handle case comprises a tube tip comprising an undercut on its inner surface.

14. The device of claim 13 wherein said means for attaching said actuator to said cartridge located at said distal portion of said handle case comprises a tube tip comprising an undercut on its inner surface.

15. A device for inserting a medicament within a body cavity of a mammal, said device comprising:
    a cartridge for containing said medicament therein, said cartridge comprising,
        a housing comprising a proximal portion and a distal portion,
        a retractable chamber disposed within said housing, said retractable chamber comprising an internal surface, an external surface and a lumen defined by said internal surface, a substantially stationary member disposed within said lumen of said retractable chamber, said substantially stationary member having a uniform cross-section sized to provide a sliding fit within said lumen to provide for retraction of said retractable chamber about said substantially stationary member upon actuation of said device; and a spring disposed about said retractable chamber for retracting said retractable chamber about said substantially stationary member while maintaining said substantially stationary member in a substantially stationary position upon actuation of said device; and an actuator for placing said device in operation, said actuator comprising, means for retracting said spring disposed about said retractable chamber about said substantially stationary member while maintaining said substantially stationary member in a substantially stationary position upon actuation of said device; and a handle case comprising and a tube tip located at a distal portion of said handle case, said tube tip comprising an undercut on its inner surface for attaching said actuator to said cartridge, wherein said proximal portion of said housing comprises flanges for engaging said undercut of said tube tip for connecting said cartridge to said actuator, and wherein said proximal portion of said housing is connected to said distal portion of said handle case, whereby said cartridge and said actuator are connected in operational engagement.

* * * * *